United States Patent
Furuhashi et al.

(10) Patent No.: US 7,679,879 B2
(45) Date of Patent: Mar. 16, 2010

(54) AIR CONDITIONING APPARATUS

(75) Inventors: Kenji Furuhashi, Hirakata (JP); Takashi Kohama, Yao (JP)

(73) Assignee: Sharp Kabushiki Kaisha, Osaka (JP)

( * ) Notice: Subject to any disclaimer, the term of this patent is extended or adjusted under 35 U.S.C. 154(b) by 346 days.

(21) Appl. No.: 11/631,935

(22) PCT Filed: Aug. 4, 2005

(86) PCT No.: PCT/JP2005/014296

§ 371 (c)(1),
(2), (4) Date: Jan. 9, 2007

(87) PCT Pub. No.: WO2006/018978

PCT Pub. Date: Feb. 23, 2006

(65) Prior Publication Data

US 2008/0074824 A1    Mar. 27, 2008

(30) Foreign Application Priority Data

Aug. 20, 2004   (JP) .............................. 2004-241359

(51) Int. Cl.
*H01T 23/00* (2006.01)
(52) U.S. Cl. ...................................... 361/231
(58) Field of Classification Search .................. 361/231
See application file for complete search history.

(56) References Cited

U.S. PATENT DOCUMENTS

| | | | | |
|---|---|---|---|---|
| 4,499,031 A | * | 2/1985 | Sexton et al. ................. | 261/66 |
| 4,686,069 A | * | 8/1987 | Hahne et al. .................. | 261/92 |
| 5,743,465 A | * | 4/1998 | Jeong ........................... | 236/51 |
| 6,985,346 B2 | * | 1/2006 | Kraz et al. ................... | 361/230 |
| 2003/0086813 A1 | | 5/2003 | Fleischer | |
| 2004/0023094 A1 | * | 2/2004 | Hatayama et al. ............. | 429/34 |

FOREIGN PATENT DOCUMENTS

| | | |
|---|---|---|
| GB | 2 254 447 A | 10/1992 |
| JP | 2000-81227 A | 3/2000 |
| JP | 2002-89932 A | 3/2002 |
| JP | 2002-203657 A | 7/2002 |
| JP | 2002-286356 A | 10/2002 |
| JP | 2003-56878 A | 2/2003 |
| JP | 2003-83593 A | 3/2003 |
| JP | 2004-150734 A | 5/2004 |
| JP | 2004-181999 A | 7/2004 |
| JP | 2004-232941 A | 8/2004 |

* cited by examiner

*Primary Examiner*—Stephen W Jackson
*Assistant Examiner*—Ann T Hoang
(74) *Attorney, Agent, or Firm*—Birch, Stewart, Kolasch & Birch, LLP

(57) ABSTRACT

An air cleaner includes an ion generator arranged in a path from an inlet port to an outlet port, a humidifying filter arranged in the path at a position closer to the inlet port than the ion generator, a dust sensor and an odor sensor for detecting impureness of air, and a temperature sensor and a humidity sensor. When impureness is detected by the dust sensor and the odor sensor and when the temperature and the humidity attain a specific state (YES at S06 to S08), a fan motor is driven such that water is supplied to the ion generator in an amount larger than when the specific state is not attained (S14).

9 Claims, 19 Drawing Sheets

| REGION | | TEMPERATURE RANGE T | HUMIDITY RANGE H |
|---|---|---|---|
| ENVIRONMENT IN WHICH VIRUSES TEND TO BE ACTIVE | REGION ① | 34°C ≧ T ≧ 24°C | 25% ≧ H ≧ 0% |
| | REGION ② | 24°C ≧ T ≧ 0°C | 40% ≧ H ≧ 0% |
| | REGION ③ | 13°C ≧ T ≧ 0°C | 100% ≧ H ≧ 40% |
| ENVIRONMENT IN WHICH ALLERGENS ARE LIKELY TO FLOAT | REGION ② | 24°C ≧ T ≧ 0°C | 40% ≧ H ≧ 0% |

F I G. 5

| ODOR SENSOR OUTPUT LEVEL | DUST SENSOR OUTPUT LEVEL | RESULT OF ADDITION OF VALUES FROM BOTH SENSORS | IMPURENESS LEVEL |
|---|---|---|---|
| 0 | 0 | 0 | 0 |
| 1 | 0 | 1 | 1 |
| 0 | 1 | 1 | |
| 1 | 1 | 2 | |
| 2 | 0 | 2 | |
| 0 | 2 | 2 | |
| 2 | 1 | 3 | |
| 1 | 2 | 3 | |
| 3 | 0 | 3 | 2 |
| 0 | 3 | 3 | |
| 3 | 1 | 4 | |
| 1 | 3 | 4 | |
| 2 | 2 | 4 | |
| 3 | 2 | 5 | |
| 2 | 3 | 5 | |
| 3 | 3 | 6 | |

F I G. 6

| ION GENERATOR DRIVE MODE | FAN MOTOR OUTPUT | | VOLTAGE APPLIED TO ION GENERATOR | | |
|---|---|---|---|---|---|
| | FAN LEVEL NOTCH | | DUTY | TIME PERIOD OF ON | CYCLE |
| CLEAN | SILENT | FAN LEVEL 1 | 10% | 1 | 10 |
| | MINIMUM | FAN LEVEL 2 | 10% | 1 | 10 |
| | LOW | FAN LEVEL 3 | 10% | 1 | 10 |
| | MEDIUM | FAN LEVEL 4 | 50% | 5 | 10 |
| | HIGH | FAN LEVEL 5 | 50% | 5 | 10 |
| | MAXIMUM | FAN LEVEL 6 | 50% | 5 | 10 |
| MONITOR | SILENT | FAN LEVEL 1 | 20% | 2 | 10 |
| | MINIMUM | FAN LEVEL 2 | 20% | 2 | 10 |
| | LOW | FAN LEVEL 3 | 20% | 2 | 10 |
| | MEDIUM | FAN LEVEL 4 | 100% | 10 | 10 |
| | HIGH | FAN LEVEL 5 | 100% | 10 | 10 |
| | MAXIMUM | FAN LEVEL 6 | 100% | 10 | 10 |
| ION CONTROL | SILENT | FAN LEVEL 1 | 20% | 2 | 10 |
| | MINIMUM | FAN LEVEL 2 | 20% | 2 | 10 |
| | LOW | FAN LEVEL 3 | 20% | 2 | 10 |
| | MEDIUM | FAN LEVEL 4 | 100% | 10 | 10 |
| | HIGH | FAN LEVEL 5 | 100% | 10 | 10 |
| | MAXIMUM | FAN LEVEL 6 | 100% | 10 | 10 |

FIG. 7

| IMPURENESS LEVEL [IMPURENESS LEVEL EVALUATION] | FAN MOTOR ||
| --- | --- | --- |
| | FAN LEVEL NOTCH ||
| | NORMAL STATE | SPECIFIC STATE |
| IMPURENESS NOT-DETECTED | FAN LEVEL 3 | FAN LEVEL 4 |
| 0 | FAN LEVEL 1 | FAN LEVEL 1 |
| 1 | FAN LEVEL 3 | FAN LEVEL 4 |
| 2 | FAN LEVEL 5 | FAN LEVEL 6 |

FIG. 8

| FAN LEVEL NOTCH | SILENT | — | MEDIUM | — | HIGH | MAXIMUM |
| --- | --- | --- | --- | --- | --- | --- |
| | FAN LEVEL 1 | FAN LEVEL 2 | FAN LEVEL 3 | FAN LEVEL 4 | FAN LEVEL 5 | FAN LEVEL 6 |
| FAN LEVEL ($m^3$/min) | 0.7 | 1.3 | 2.2 | 3.2 | 4.1 | 5.1 |
| AMOUNT OF HUMIDIFICATION (cc/h) | 60 | 70 | 100 | 135 | 165 | 200 |

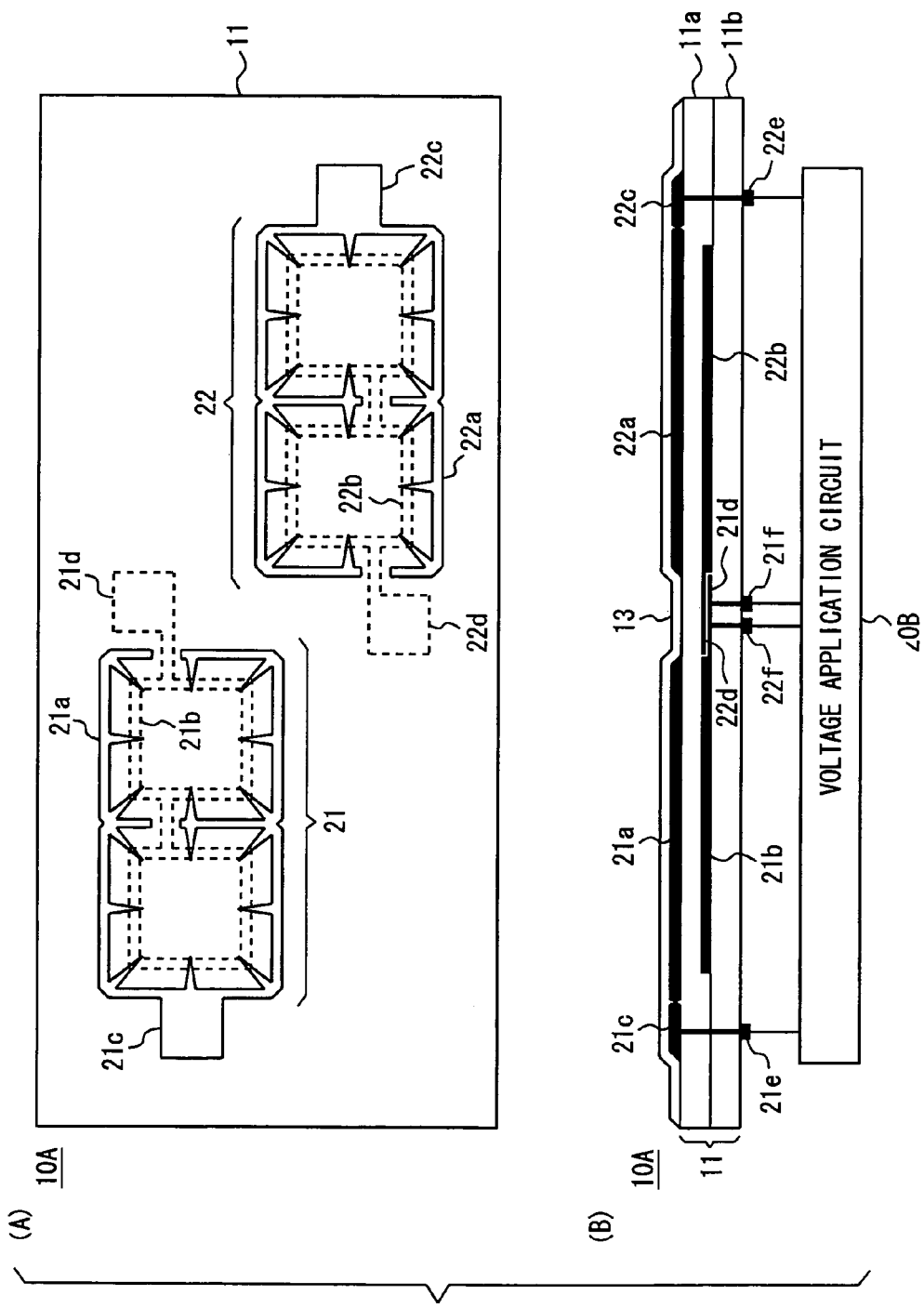

AIR CONDITIONING APPARATUS

TECHNICAL FIELD

The present invention relates to an air conditioning apparatus, and more particularly to an air conditioning apparatus for sterilizing air in a room.

BACKGROUND ART

An ion generator ionizing vapor present in a space has conventionally been known. Some of the ion generators employ creeping discharge. In the conventional ion generator, when an alternating voltage is applied to an ion generating element, positive ions and negative ions are generated. It is known that these generated positive and negative ions eliminate molds, airborne fungi or viruses in the air.

Japanese Patent Laying-Open No. 2003-083593 (Patent Document 1) discloses a technique to apply such an ion generator to an air conditioner so as to suppress molds. The air conditioner disclosed in Japanese Patent Laying-Open No. 2003-083593 generates positive and negative ions from the ion generator, and determines whether or not dehumidification or cooling/heating should be performed in accordance with detected temperature or humidity in the room.

The air conditioner disclosed in Japanese Patent Laying-Open No. 2003-083593 generates positive and negative ions from the ion generator whenever it is driven. Therefore, a constant amount of positive and negative ions is generated regardless of the temperature or humidity in the room.

In general, among the viruses, influenza virus is known to attain a high survival rate at low temperature and low humidity. Accordingly, in an environment in which viruses are more likely to proliferate, concentration of ions in the room should desirably be higher than in an environment in which viruses are less likely to proliferate.

[Patent Document 1] Japanese Patent Laying-Open No. 2003-083593

Disclosure of the Invention

Problems to be Solved by the Invention

The present invention was made to solve the above-described problems. An object of the present invention is to provide an air conditioning apparatus capable of efficiently killing airborne fungi in a room.

Means for Solving the Problems

In order to achieve the above-described objects, according to one aspect of the present invention, an air conditioning apparatus includes: an ion generation portion arranged in a path from an inlet port to an outlet port and generating ions; a humidifying portion arranged in the path at a position closer to the inlet port than the ion generation portion and humidifying air; an impureness detection portion for detecting impureness of air; a temperature and humidity detection portion detecting temperature and humidity; and a control unit controlling the humidifying portion such that, when impureness is detected by the impureness detection portion and when the temperature and the humidity detected by the temperature and humidity detection portion attain a prescribed state, water is supplied to the ion generation portion in an amount larger than when the prescribed state is not attained.

According to the present invention, the humidifying portion is arranged in the path from the inlet port to the outlet port at a position closer to the inlet port than the ion generation portion. When impureness is detected and when the temperature and the humidity attain a prescribed state, water is supplied to the ion generation portion in an amount larger than when the prescribed state is not attained. Here, ions are surrounded by water molecules, whereby its residual period is extended. Therefore, an air conditioning apparatus achieving improvement in sterilizing effect by supplying a larger amount of water to the ion generation portion so as to extend the residual period of ions can be provided.

Preferably, the humidifying portion includes a blowing portion causing air to flow such that the air taken in through the inlet port exits through the outlet port, a tray for holding water, and a filter partially immersed in the water held in the tray. The control unit controls the blowing portion to raise the fan level.

According to the present invention, the fan level is raised to increase an amount of air that passes through the filter. Therefore, an amount of vaporized water is increased. With such a simplified structure for raising the fan level, an amount of water supplied to the ion generation portion can be controlled.

Preferably, when impureness is detected by the impureness detection portion and when the temperature and the humidity detected by the temperature and humidity detection portion attain the prescribed state, the control unit controls the ion generation portion to generate ions in an amount larger than when the prescribed state is not attained.

According to the present invention, in the prescribed state, ions are generated in an amount larger than when the prescribed state is not attained, and a large amount of water is supplied. Therefore, the residual period of ions can be extended.

Preferably, the air conditioning apparatus further includes a state notification portion for notification of the temperature detection result and/or the humidity detection result, and an instruction accepting portion accepting an instruction to start control of the humidifying portion. The humidifying portion starts control in response to acceptance of the instruction by the instruction accepting portion.

According to the present invention, if a user desires, an amount of ions in the room can be increased.

Preferably, the ion generation portion generates positive ions and negative ions.

Preferably, the prescribed state includes a state in which viruses are likely to proliferate.

Preferably, the impureness detection portion includes a dust sensor.

Preferably, the impureness detection portion includes an odor sensor.

Preferably, the air conditioning apparatus further includes a cleaning portion for lowering impureness level of air.

BRIEF DESCRIPTION OF THE DRAWINGS

FIG. 5 shows an exemplary impureness level evaluation table.

FIG. 6 shows relation between a fan motor output and a voltage applied to the ion generator for each drive mode of the ion generator.

FIG. 7 shows an exemplary fan level determination table in an automatic mode.

FIG. 8 shows relation between the fan level and an amount of humidification.

FIG. 22 shows a variation of the ion generator.

DESCRIPTION OF THE REFERENCE CHARACTERS

Figure 1:
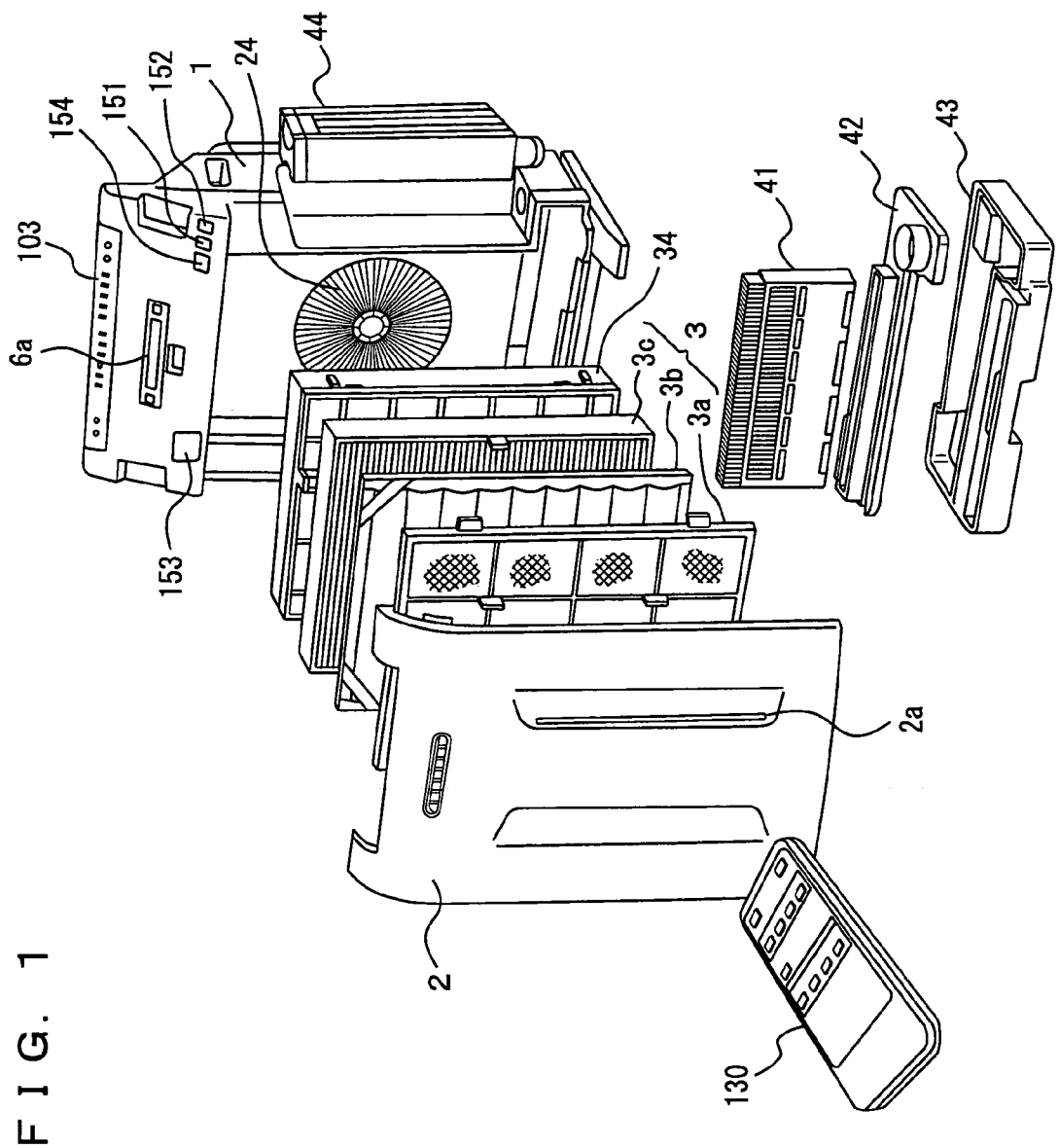
FIG. 1 is an exploded perspective view of an air cleaner incorporating an ion generator.

1 air cleaner main unit; 2a inlet port; 6a, 6b outlet port; 10, 10A ion generator; 20, 20a, 20b voltage application circuit; 103 operation portion; 104 operation switch button; 115 monitor indicator light; 130 remote controller; 150 control unit; 151 temperature sensor; 152 humidity sensor; 153 dust sensor; and 154 odor sensor.

BEST MODES FOR CARRYING OUT THE INVENTION

In the following, an embodiment of the present invention will be described with reference to the drawings. It is noted that the same reference characters refer to the same or corresponding components and denotation and functions thereof are also the same. Therefore, detailed description thereof will not be repeated.

Figure 2:
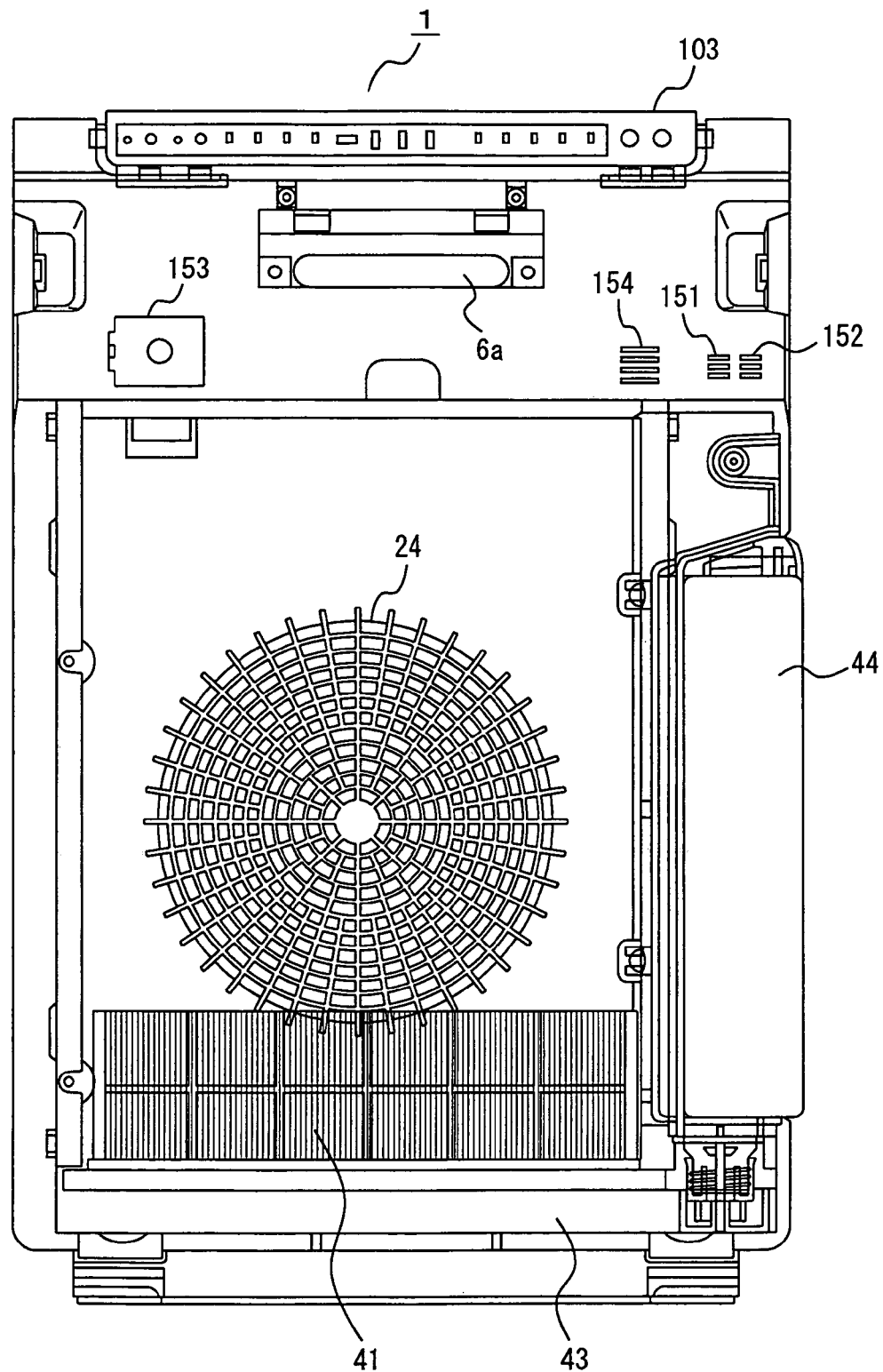
FIG. 2 is a front view of an air cleaner main unit.
Figure 3:
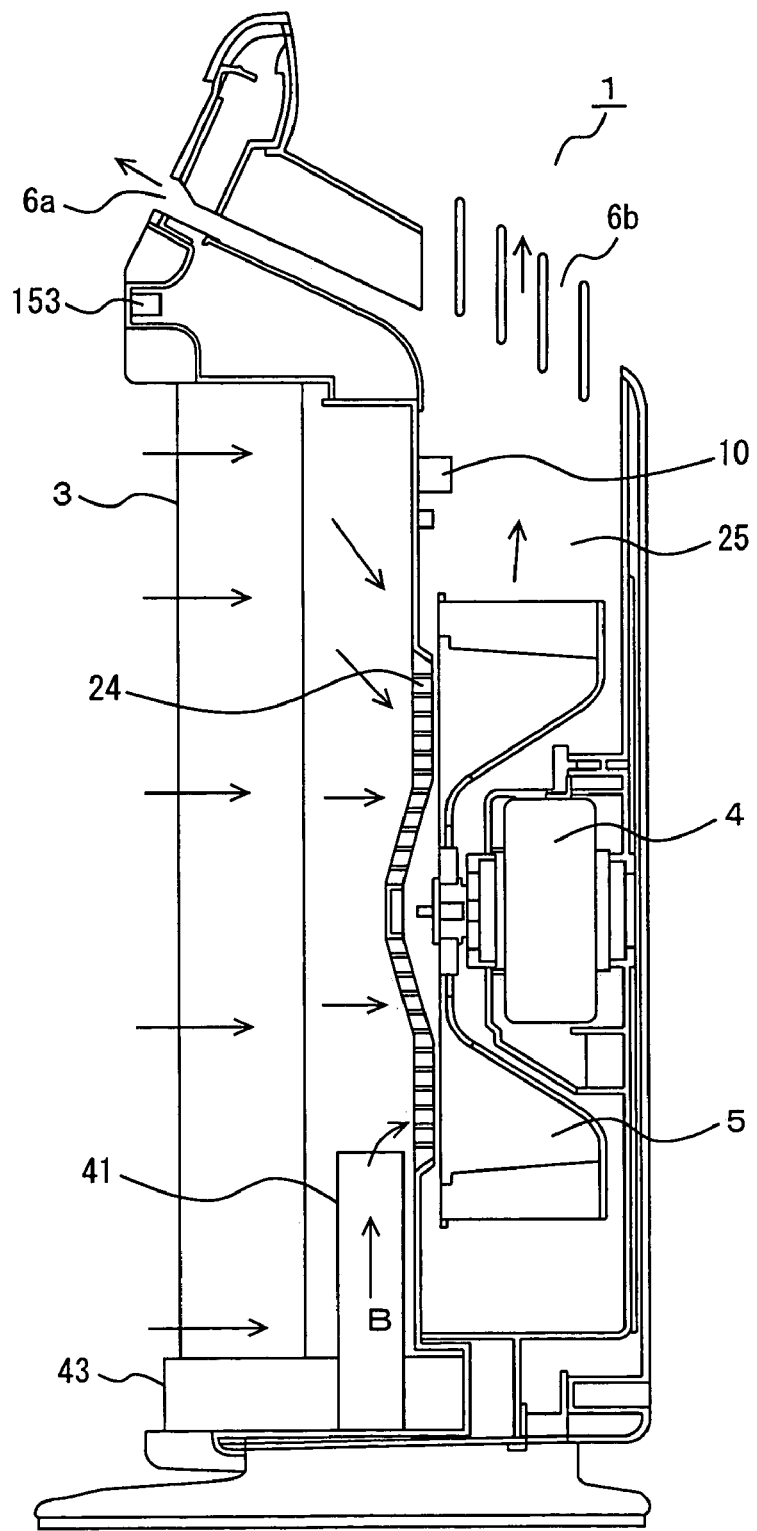
FIG. 3 is a cross-sectional view of the air cleaner main unit.

FIG. 1 is an exploded perspective view of an air cleaner incorporating an ion generator, FIG. 2 is a front view of a main unit of the air cleaner in FIG. 1, and FIG. 3 is a cross-sectional view of the main unit of the air cleaner in FIG. 1.

As shown in FIGS. 1 to 3, the air cleaner incorporating the ion generator includes a main unit 1 of the air cleaner, a front panel 2 of the main unit, a filter portion 3 consisting of a plurality of types of filters, a fan motor 4, a turbo fan 5, a tank 44, a humidifying filter 41, a first outlet port 6a, a second outlet port 6b, an ion generator 10, an operation portion 103 attaining a function to display an operation status, an inlet port 2a in front panel 2, and a remote controller 130 operated in order to send a signal for remote control of an operation of the air cleaner to operation portion 103.

Main unit 1 of the air cleaner is structured such that front panel 2 is provided to cover a part of the front face of main unit 1.

When viewed from the front, main unit 1 has a rectangular opening serving as a housing implemented by a hollow portion for housing filter portion 3. Holes 24 for passing the air that has passed through filter portion 3 are radially formed on a bottom surface of the housing. Behind radial holes 24, turbo fan 5 and fan motor 4 for rotating the turbo fan are disposed. Above turbo fan 5, first outlet port 6a and second outlet port 6b for releasing the air to the room are provided. Ion generator 10 is arranged at some position in an airflow path 25 above turbo fan 5.

Front panel 2 is attached in such a manner that it is engaged to main unit 1 with a prescribed gap therefrom, and inlet port 2a for taking the air into the room is formed in a central portion in a vertically extending manner. Front panel 2 may be attached to main unit 1 such that the air in the room is taken in also through a gap between front panel 2 and main unit 1.

As shown in FIG. 1, filter portion 3 consists of three types of filters; a prefilter 3a, a deodorizing filter 3b, and a dust collection filter 3c. These filters are housed in the hollow portion on the front face of main unit 1 in such a manner that they are housed in a filter frame 34 in that order from a side of inlet port 2a. Prefilter 3a collects large particles of dust or dirt, deodorizing filter 3b adsorbs odorous substances such as acetaldehyde, ammonia, acetic acid or the like, and dust collection filter 3c collects dust or dirt in the air with a HEPA sheet.

Filter portion 3 is structured in the above-described manner, such that prefilter 3a collects dust or dirt in the air in the room that has been taken in, deodorizing filter 3b adsorbs odorous substances in the air such as acetaldehyde, ammonia, acetic acid or the like, and finally dust collection filter 3c collects fine dust or dirt that has passed through prefilter 3a. Therefore, the air that has been filtered through filter portion 3 has the odor and the dust or dirt eliminated.

Fan motor 4 rotating turbo fan 5 for taking in the air in the room is arranged downstream of filter portion 3. Turbo fan 5 has a blade extending in a radial direction and bent rearward. Turbo fan 5 formed in such a manner attains highest static pressure and silence. Placing importance on controllability, a direct-current motor is used as fan motor 4. Fan motor 4 in the present embodiment can switch the fan level in six levels.

In one side portion of air cleaner main unit 1, removable tank 44 for storing water is accommodated. A water feed port in a lower portion of tank 44 is connected to a tray 43. The water stored in tank 44 flows through the water feed port to tray 43, and is supplied to tray 43. The water stored in tray 43 has the surface maintained at a prescribed level.

Humidifying filter 41 is supported by an upper cover 42 covering an upper surface of tray 43. A lower portion of humidifying filter 41 is partially immersed in the water stored in tray 43. Humidifying filter 41 is arranged downstream of filter portion 3 and upstream of turbo fan 5. Humidifying filter 41 is disposed at a position closer to inlet port 2a than ion generator 10.

Humidifying filter 41 absorbs water stored in tray 43 and becomes wet. When humidifying filter 41 is blown by the wind in such a state, the water contained in humidifying filter 41 is vaporized. When turbo fan 5 rotates, the air flows and the air is taken in through inlet port 11a. A part of the air that has passed through filter portion 3 passes through humidifying filter 41, and is transported to ion generator 10. Thereafter, the air exits through first outlet port 6a or second outlet port 6b to the room.

Air cleaner main unit 1 has a temperature sensor 151, a humidity sensor 152, a dust sensor 153, and an odor sensor 154 above the housing for housing filter portion 3. Dust sensor 153 is a particle sensor for detecting an airborne particle. Odor sensor 154 is a well-known sensor utilizing such a characteristic that a resistance value is varied when a gas component adsorbs on a surface of the sensor implemented by a metal oxide semiconductor.

An operation mode of the air cleaner will now be described. The air cleaner can be driven in five operation modes of an automatic mode, a 15-minute high-fan-level mode, a pollen mode, a silent mode, and a quick mode. The automatic mode refers to an operation mode in which ion generator 10 and fan motor 4 are controlled based on temperature, humidity and impureness level detected by temperature sensor 151, humidity sensor 152, dust sensor 153, and odor sensor 154. The automatic mode will be described in detail later.

The 15-minute high-fan-level mode, the pollen mode, the silent mode, and the quick mode represent a drive mode of fan motor 4, that is, an operation mode in which fan motor 4 is controlled to vary the fan level in terms of time. In the 15-minute high-fan-level mode, turbo fan 5 is driven at a high fan level for 15 minutes (fan level ) and thereafter the mode is switched to the automatic mode. In the pollen mode, for example, turbo fan 5 operates at a fan level "high (fan level 5)" for 10 minutes, and thereafter repeats the operation at fan level "medium (fan level 4)" and fan level "high (fan level 5)". In the silent mode, turbo fan 5 supplies breezy wind and the operation is quiet. In the quick mode, turbo fan 5 operates at fan level "maximum (fan level 6)".

The drive mode of ion generator 10 includes an ion control mode and a clean mode. The ion control mode refers to a mode in which negative ions in an amount larger than that of positive ions are generated from ion generator 10, or to a mode in which solely negative ions are generated. The clean mode refers to a mode in which positive ions and negative ions are generated in a substantially equal amount from ion generator 10.

In the automatic mode, the impureness level is calculated based on outputs from dust sensor 153 and odor sensor 154, and the fan level is determined based on the impureness level. In addition, whether or not the temperature and the humidity detected by temperature sensor 151 and humidity sensor 152 attain a specific state is determined. The drive mode of ion generator 10 is determined based on whether the temperature and the humidity attain the specific state and on the impureness level. If the impureness level is lowest and the temperature and the humidity do not attain the specific state, the ion control mode is set. Otherwise, the clean mode is set. In addition, if the temperature and the humidity attain the specific state, a monitor mode is set.

The clean mode out of the drive modes of ion generator 10 includes the monitor mode. The monitor mode is one type of the clean mode. A monitor purification mode refers to a drive mode of ion generator 10 when the temperature detected by temperature sensor 151 and the humidity detected by humidity sensor 152 attain the specific state. Here, a state in which the temperature detected by temperature sensor 151 and the humidity detected by humidity sensor 152 do not attain the specific state is referred to as a normal state. The drive mode of ion generator 10 is set to the monitor mode when the temperature and the humidity attain the specific state, in which case, positive and negative ions are generated in an amount larger than in the normal state.

Figures 4A, 4B:
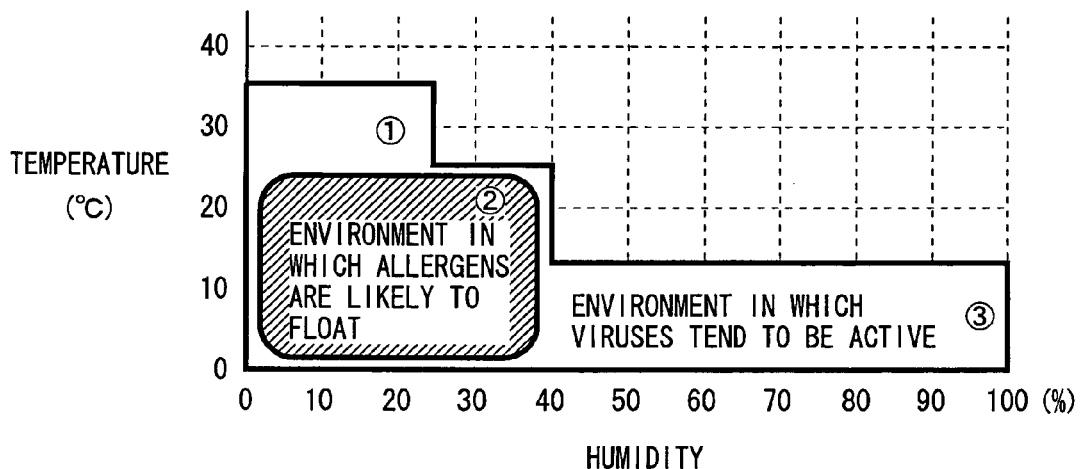
FIG. 4A shows one example of a specific state.
FIG. 4B shows one example of a specific state.

Referring to FIGS. 4A and 4B, the ordinate represents temperature and the abscissa represents humidity, thereby representing a region determined by the temperature and the humidity. The specific state includes a first region where the temperature is not lower than 24° C. and not higher than 34° C. and the humidity is not lower than 0% and not higher than 25%, a second region where the temperature is not lower than 0° C. and not higher than 24° C. and the humidity is not lower than 0% and not higher than 40%, and a third region where the temperature is not lower than 0° C. and not higher than 13° C. and the humidity is not lower than 40% and not higher than 100%. The first to third regions represent regions where viruses tend to be active. In particular, the second region represents an environment where allergens are likely to float.

FIG. 5 shows an exemplary impureness level evaluation table. The impureness level evaluation table is stored in advance in a read-only memory (ROM) of the air cleaner. Referring to FIG. 5, the impureness level evaluation table associates odor sensor output levels, dust sensor output levels and results of addition of values from both sensors with the impureness level for storage. In the present embodiment, output levels of odor sensor 154 ranges from 0 to 3, while output levels of dust sensor 153 ranges from 0 to 3. That is, an amount of odor and dust is output in 4 levels. As the value for odor sensor output level becomes larger, it indicates that an amount of substance in the air causing the odor is larger. Meanwhile, as the value for dust sensor output level becomes larger, an amount of dust in the air is larger. The addition result represents the sum of the odor sensor output level and the dust sensor output level. The addition result ranges from 0 to 6.

The impureness level is associated with the odor sensor output level and the dust sensor output level. Even when the addition results are the same, the impureness level may be different. For example, when the odor sensor output level attains to 1 and the dust sensor output level attains to 2, the addition result is 3 and this example is associated with the impureness level of 1. On the other hand, when the odor sensor output level attains 3 and the dust sensor output level attains 0, this example is associated with the impureness level of 2 in spite of the addition result of 3. This is because the odor sensor output level attains to 3, which indicates that an amount of substance causing odor is largest. In such a case, the impureness level is determined as 2, not 1.

Though the impureness level has ranged in 3 levels of 0 to 2 here, the impureness level is not limited to such an example. A larger or smaller number of levels may be set, and two levels may be set, for example. In addition, though the impureness level has been detected based on the output values from two sensors of odor sensor 154 and dust sensor 153 in the present embodiment, any one sensor output may be used to detect the impureness level.

FIG. 6 shows relation between a fan motor output and a voltage applied to the ion generator for each drive mode of the ion generator. Here, the voltage applied to ion generator 10 when duty is varied is exemplarily shown. Referring to FIG. 6, when the drive mode is set to the clean mode and when comparison is made between in the monitor mode and not in the monitor mode, duty is larger in the monitor mode, even though the fan level is the same. Therefore, positive and negative ions are generated in an amount larger than when not in the monitor mode. If the drive mode of the ion generator is set to the clean mode, it is the positive and negative ions that are generated from ion generator 10. Meanwhile, in the ion control mode, negative ions are generated from ion generator 10 in an amount larger than that of positive ions.

It is noted that an amount of ions generated from ion generator 10 in the present embodiment refers to a ratio between positive ions and negative ions in the air, and relates to the output of fan motor 5. Here, the output of fan motor 5 is represented by the fan level, which is categorized into 6 levels from fan level 1 to fan level 6. Fan speed is higher at fan level 6 than at fan level 1.

When an applied voltage duty increases, generated discharge noise also becomes greater. Accordingly, when the fan motor output is low and wind noise is low, the discharge noise from the ion generator is preferably also low. Therefore, by changing the applied voltage duty in accordance with the fan motor output, silent operation of an entire product can be realized.

When the fan speed is low, the wind noise is also low. In order to lower overall operation noise, the discharge noise from the ion generator and the voltage duty are preferably low. In contrast, when the fan speed is high, the wind noise is also great. Therefore, even if the discharge noise from the ion generator is great, it does not considerably affect the overall operation noise. Therefore, by setting duty 100% at fan level 5 or 6, quietness and desired ion concentration can be realized without much affecting the overall operation noise.

A fan level in the automatic mode and the drive mode of the ion generator will now be described.

FIG. 7 shows an exemplary fan level determination table in the automatic mode. In the automatic mode, the fan level is determined based on the impureness level.

When the impureness level is determined as "0", fan level 1 is set for both of the normal state and the specific state. When the impureness level is determined as "1", fan level 3 is set for the normal state and fan level 4 is set for the specific state. When the impureness level is determined as "2", fan level 5 is set for the normal state and fan level 6 is set for the specific state.

If impureness is detected, that is, when the impureness level is determined as at least 1, the fan level in the specific state is set to be higher than the fan level in the normal state. This is because, the larger an amount of water supplied to ion generator 10 is, the longer the residual period of generated cluster ions is. When the fan level is raised, an amount of air that passes through humidifying filter 41 is increased, whereby a larger amount of water is vaporized. Therefore, an amount of water supplied to ion generator 10 is increased.

FIG. 8 shows relation between the fan level and an amount of humidification. As shown in FIG. 8, it can be seen that, as the fan level is raised, the amount of humidification (the amount of vaporized water) is increased.

Figure 9:
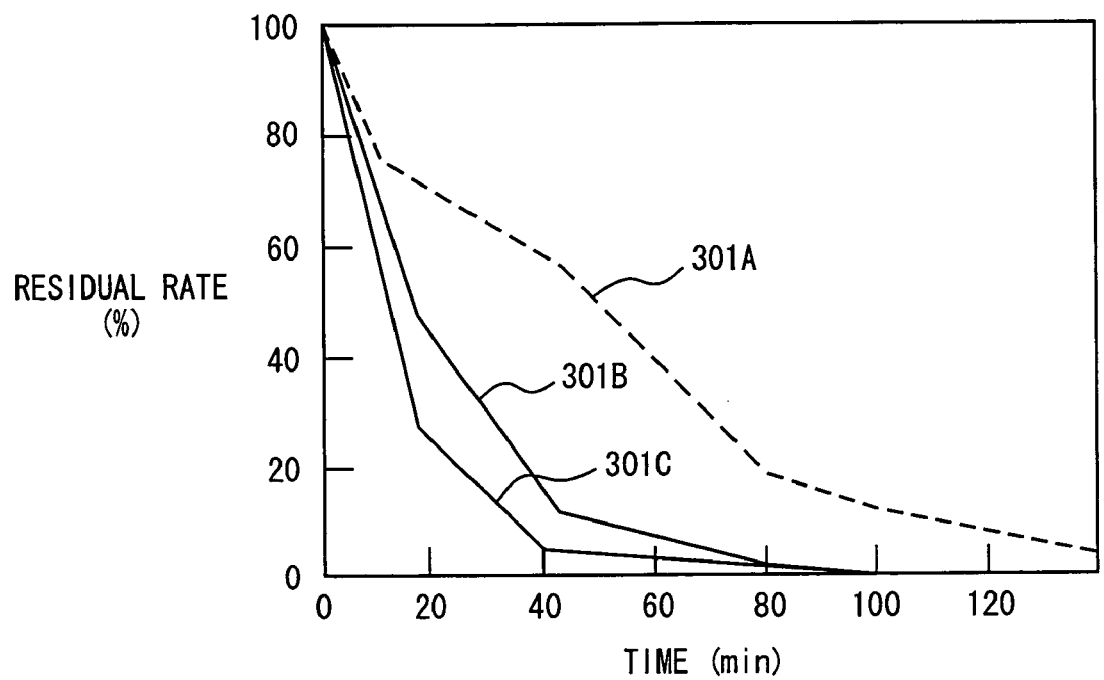
FIG. 9 shows residual rate of airborne fungi in a time-series manner.

FIG. 9 shows a residual rate of airborne fungi in a time-series manner. Referring to FIG. 9, a dotted line 301A represents a residual rate of airborne fungi in a natural state, a solid line 301B represents a residual rate of airborne fungi when positive and negative ions are generated from ion generator 10, and a solid line 301C represents a residual rate of airborne fungi when positive and negative ions are generated while humidified air is supplied to ion generator 10.

It can be seen that the case in which positive and negative ions are generated while humidified air is supplied to ion generator 10 is more effective in killing the airborne fungi than the case in which positive and negative ions are generated from ion generator 10 without humidification.

Figure 10:
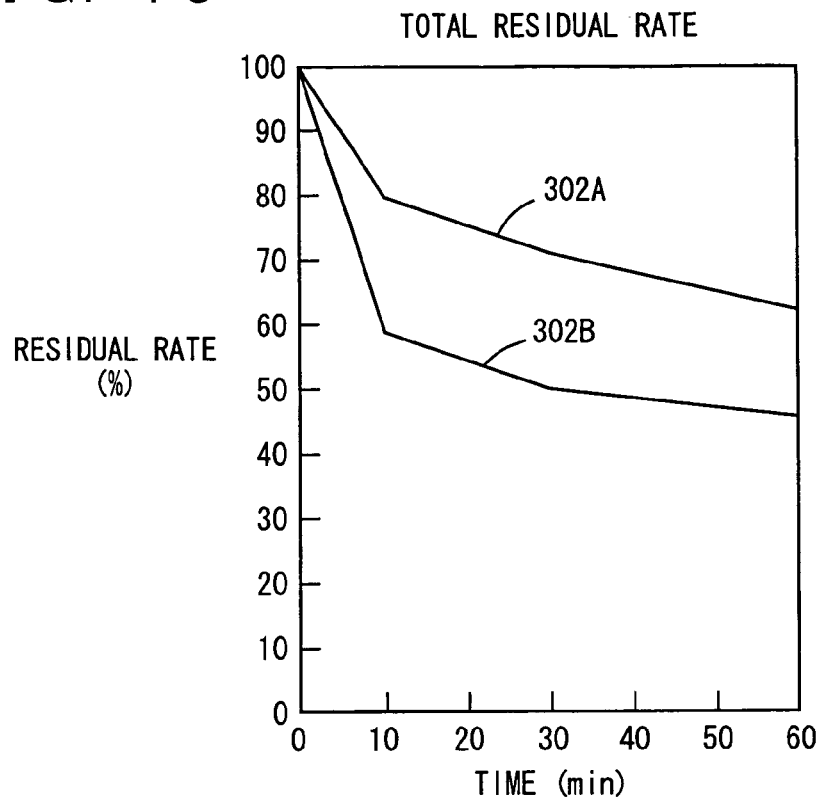
FIG. 10 is a first diagram of a result of a deodorization test.
Figure 11:
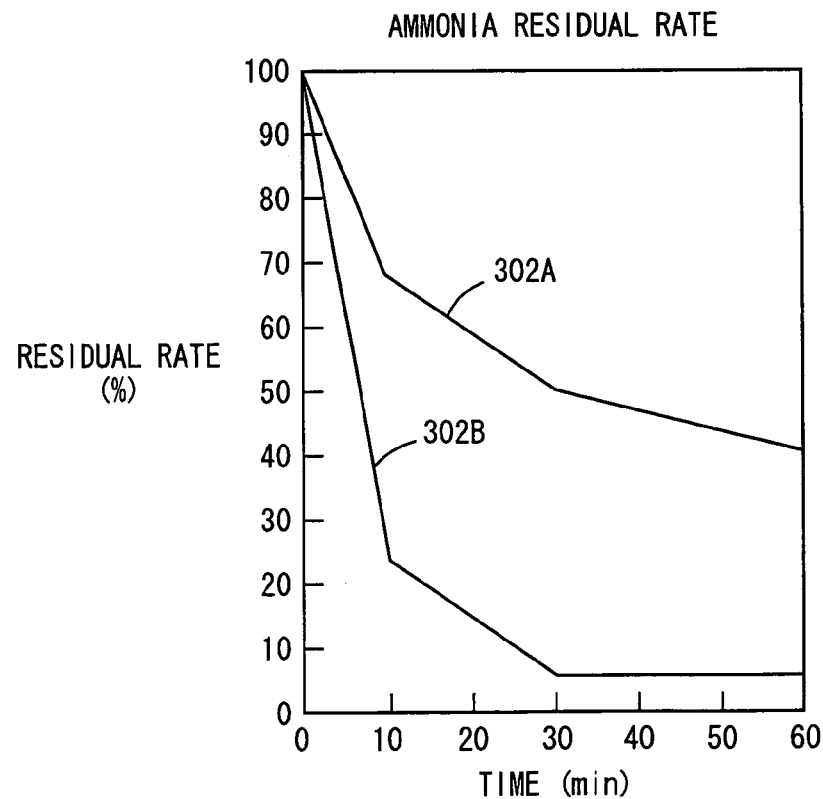
FIG. 11 is a second diagram of a result of a deodorization test.
Figure 12:
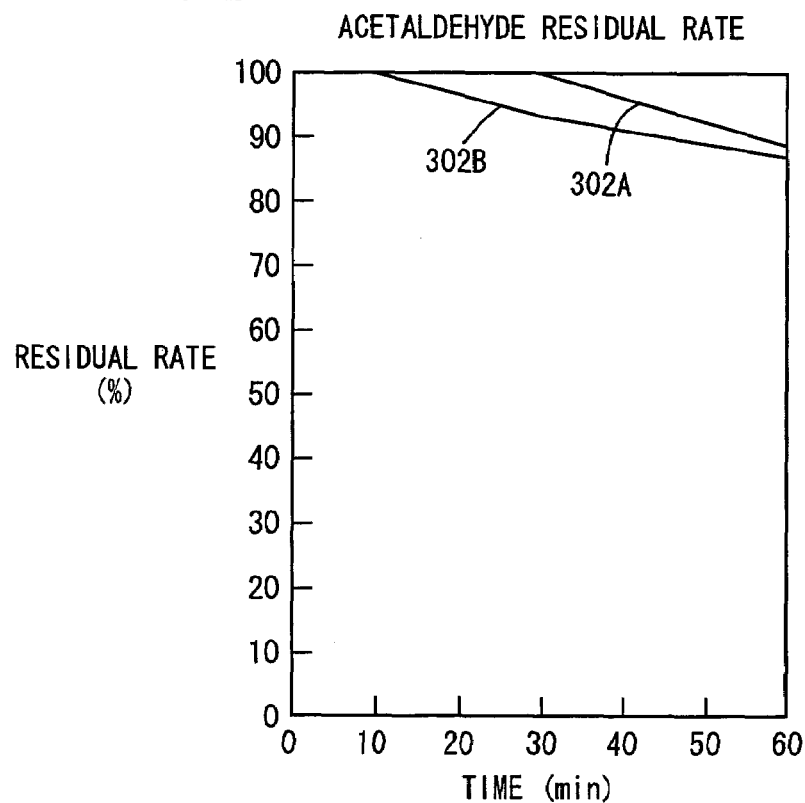
FIG. 12 is a third diagram of a result of a deodorization test.
Figure 13:
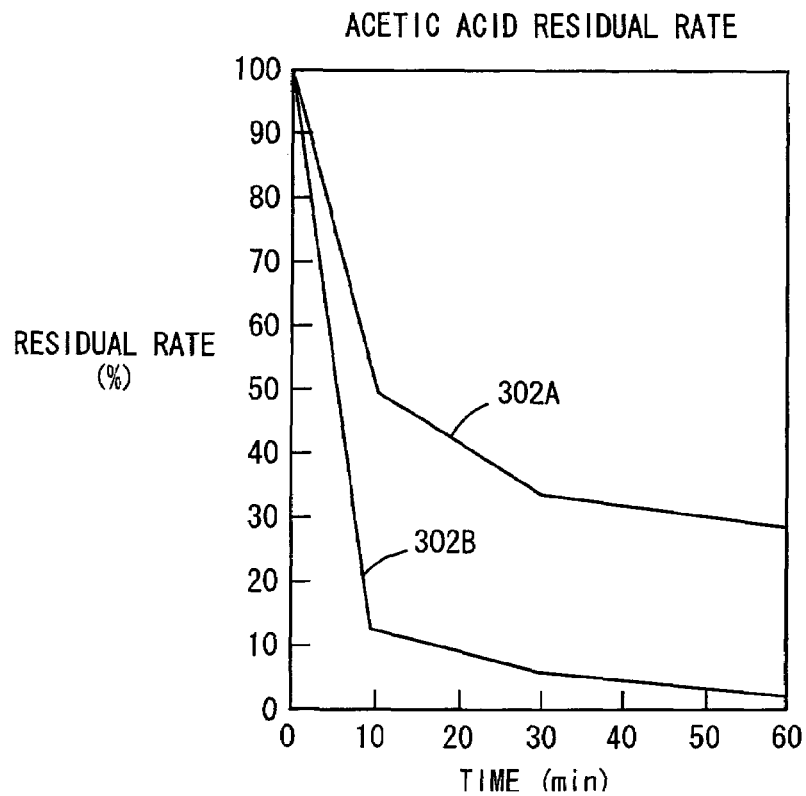
FIG. 13 is a fourth diagram of a result of a deodorization test.

FIGS. 10 to 13 show results of a deodorization test. FIG. 10 shows a test result as a whole, FIG. 11 shows a residual rate of ammonia, FIG. 12 shows a residual rate of acetaldehyde, and FIG. 13 shows a residual rate of acetic acid. A solid line 302A represents a residual rate of an odorous substance when positive and negative ions are generated from ion generator 10, and a solid line 302B represents a residual rate of an odorous substance when positive and negative ions are generated while humidified air is supplied to ion generator 10.

It can be seen that the case in which positive and negative ions are generated while humidified air is supplied to ion generator 10 is more effective in eliminating the odorous substance than the case in which positive and negative ions are generated from ion generator 10 without humidification.

Figure 14:
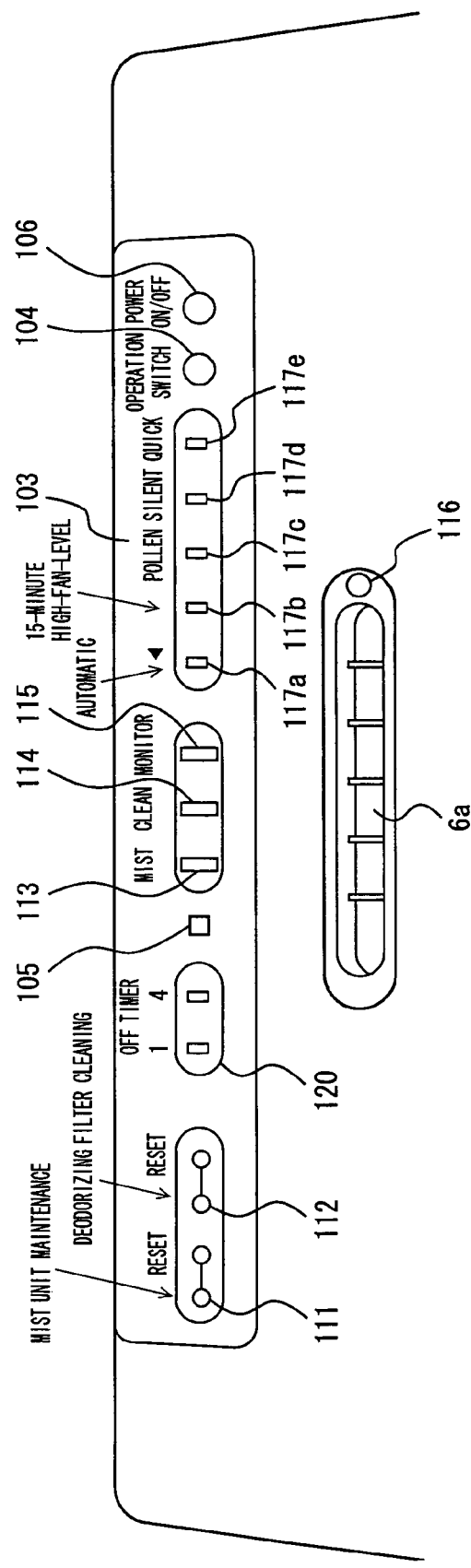
FIG. 14 is an enlarged view of an operation portion of the air cleaner.

FIG. 14 is an enlarged view of operation portion 103 of the air cleaner. Operation portion 103 includes: a power button 106 for turning on/off main unit 1; a light receiving portion 105 for receiving an infrared ray from remote controller 130; a mist unit maintenance indicator light 111 for notifying a user of a time to clean the humidifying filter; a deodorizing filter cleaning indicator light 112 for notifying the user of a time to clean filter portion 3; a mist indicator light 113 indicating an operation mode of the air cleaner; a clean sign indicator light 114 indicating impureness level of the air in the room; a monitor indicator light 115 for displaying a state of the temperature and humidity in the room; a cluster ion indicator light 116 indicating a drive state of ion generator 10; an automatic mode indicator light 117a indicating an operation mode of the air cleaner; a 15-minute high-fan-level mode indicator light 117b, a pollen mode indicator light 117c, a silent mode indicator light 117d, and a quick mode indicator light 117e; an operation switch button 104 for switching the operation mode; and an off timer indicator light 120 indicating an off-timer setting.

Operation switch button 104 is operated for switching the operation mode of main unit 1. When power button 105 is pressed, the operation is started in the automatic operation mode. Here, automatic mode indicator light 117a illuminates.

Each time operation switch button 104 is pressed, the operation mode is sequentially switched to the automatic mode, the 15-minute high-fan-level mode, the pollen mode, the silent mode, the quick mode, the automatic mode, and so on, and corresponding to the switched operation mode, the indicator light illuminates sequentially in the order of automatic mode indicator light 117a, 15-minute high-fan-level mode indicator light 117b, pollen mode indicator light 117c, silent mode indicator light 117d, quick mode indicator light 117e, automatic mode indicator light 117a, and so on.

Deodorizing filter cleaning indicator light 112 illuminates when an accumulated operation time of the air cleaner exceeds a predetermined deodorizing filter cleaning time, and otherwise it turns off. In this manner, the user can be notified of timing to clean deodorizing filter 3b. The accumulated operation time is reset to zero by means of a reset button provided next to deodorizing filter cleaning indicator light 112.

Mist unit maintenance indicator light 111 illuminates when an accumulated operation time of the air cleaner while water is contained in tank 44 and tray 43, that is, an accumulated humidifying operation time, exceeds a predetermined humidifying filter cleaning time, and otherwise it turns off. In this manner, the user can be notified of timing to clean humidifying filter 41. The accumulated operation time is reset to zero by means of a reset button provided next to mist unit maintenance indicator light 111.

Off timer indicator light 120 indicates timer setting in accordance with the instruction from the user. One of two off timer indicator lights 120 illuminates in accordance with the number of times of instruction given by the user.

Mist indicator light 113 illuminates when the water is contained in tray 43.

Clean sign indicator light 114 indicates impureness level of the air in the room. Clean sign indicator light 114 illuminates in green, corresponding to impureness level "0" indicating the lowest impureness level; it illuminates in orange, corresponding to impureness level "1" indicating an intermediate level of impureness; and it illuminates in red, corresponding to impureness level "2" indicating the highest impureness level.

Cluster ion indicator light 116 indicates a drive mode of ion generator 10. Cluster ion indicator light 116 illuminates in green when ion generator 10 operates in the ion control mode. In the clean mode, cluster ion indicator light 116 flashes in blue in a cycle of 5 seconds in the monitor mode, whereas it illuminates in blue when not in the monitor mode. When ion generator 10 is not driven, cluster ion indicator light 116 turns off.

Monitor indicator light 115 illuminates when the temperature and the humidity attain the specific state. Therefore, the user is notified that the room is in the environment where viruses are likely to proliferate. At this time point, the user operates operation switch button 104 to switch the operation mode to the automatic mode, so that the drive mode of ion generator 10 is switched to the monitor mode in the clean mode and the fan level is raised. Therefore, an amount of positive and negative ions generated from ion generator 10 is increased and an amount of water supplied to ion generator 10 is increased, whereby the residual period of generated positive and negative ions is extended. A larger amount of ions are thus released to the room and higher concentration of the positive and negative ions in the room can be achieved.

Figure 15:
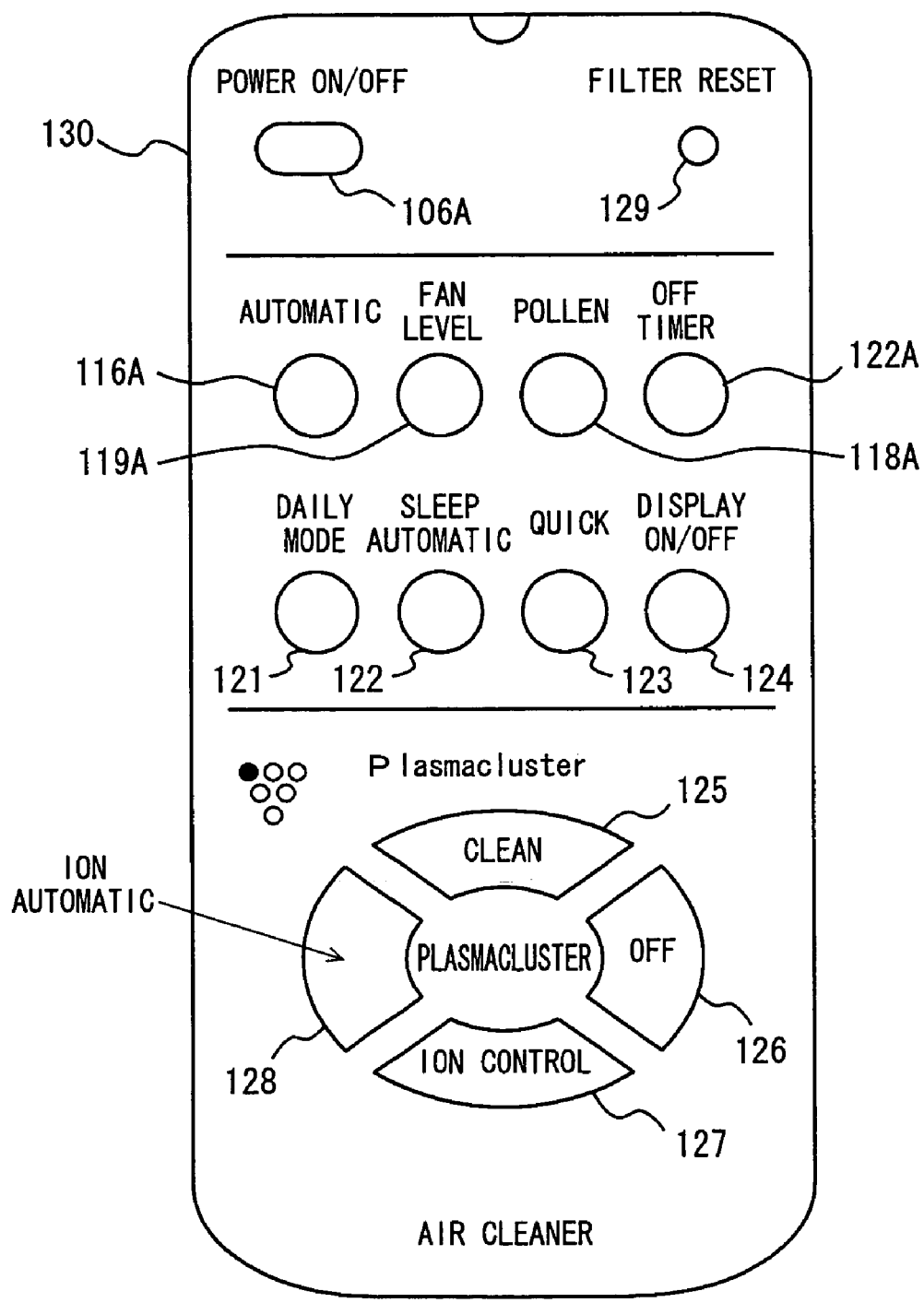
FIG. 15 is a plan view of a remote controller.

FIG. 15 is a plan view of remote controller 130. Remote controller 130 includes: a power switch 106A for turning on/off the power of the air cleaner; a filter reset button 129 for resetting the accumulated operation time after cleaning the deodorizing filter; an automatic mode button 116A for setting the operation mode of the air cleaner to the automatic mode; a fan level button 119A for switching to the manual mode and designating a fan level of fan motor 4; a pollen mode button 118A for setting the pollen mode; an off-timer button 122A for setting an off-timer; a daily mode button 121 for setting a daily mode; a sleep automatic mode button 122 for setting a sleep automatic mode; a quick mode button 123 for setting the quick mode; a display switch button 124 for switching on/off display on operation portion 103; and setting buttons 125 to 128 for manually setting the drive mode of ion generator 10.

Remote controller 130 outputs a signal of infrared ray in accordance with the pressed switch. When light receiving portion 105 in the air cleaner receives the signal of infrared ray, the air cleaner is driven in response to the signal of infrared ray.

Though remote controller 130 using the infrared ray is exemplarily described here, a communication medium between remote controller 130 and the air cleaner is not limited to the infrared ray. For example, an electromagnetic wave or an acoustic wave can be employed, and any means allowing radio communication may be used, without limited to the infrared ray.

When automatic mode button 116A is pressed, the air cleaner operates in the automatic mode. When fan level button 119A is pressed, the air cleaner changes the fan level in the order of silent, medium and maximum every time fan level button 119A is pressed. When pollen mode button 118A is pressed, the air cleaner operates in the pollen mode. Every time off-timer button 122A is pressed, the off-timer is sequentially set to either 1 hour or 4 hours.

When daily mode button 121 is pressed, the air cleaner operates in the operation mode that has been stored in advance. When sleep automatic mode button 122 is pressed, the air cleaner operates in the silent mode. When quick mode button 123 is pressed, the air cleaner operates in the quick mode.

Figure 16:
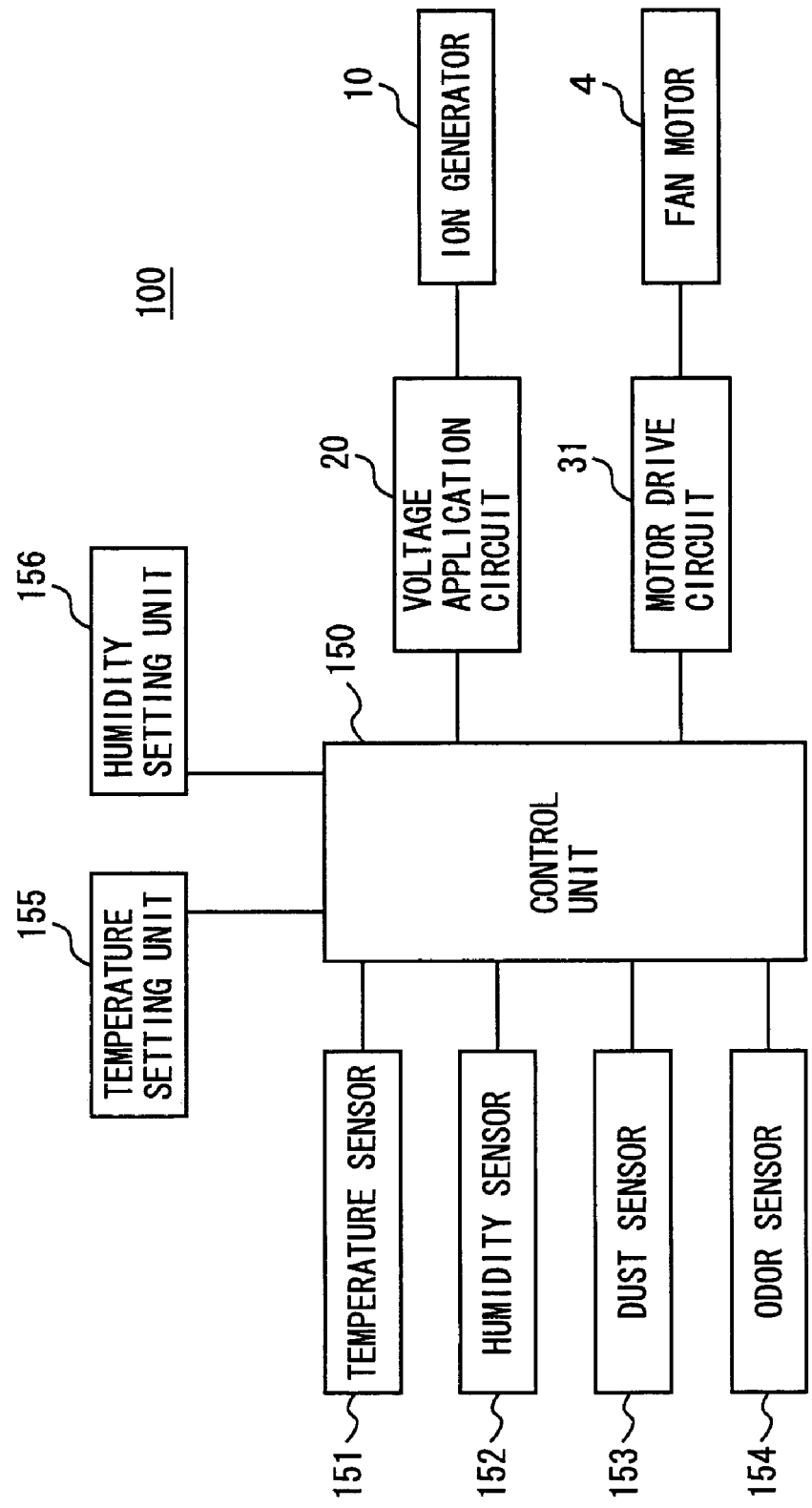
FIG. 16 is a circuit block diagram of the air cleaner in the present embodiment.

When any of setting buttons 125 to 128 is pressed, the drive mode of ion generator 10 is switched. When setting button 126 is pressed, application of a voltage to ion generator 10 is stopped so as to stop drive of ion generator 10. When setting button 125 is pressed, ion generator 10 is driven in the clean mode. When setting button 127 is pressed, ion generator 10 is driven in the ion control mode. When setting button 128 is pressed, an air cleaner 100 is driven in the automatic mode FIG. 16 is a circuit block diagram of the air cleaner in the present embodiment. Referring to FIG. 16, in the air cleaner, a control unit 150 for overall control includes temperature sensor 151, humidity sensor 152, dust sensor 153, odor sensor 154, a temperature setting unit 155 for setting temperature, a humidity setting unit 156 for setting humidity, a voltage application circuit 20 for applying a voltage to ion generator 10, and a motor drive circuit 31 for controlling drive of fan motor 4. Ion generator 10 is connected to voltage application circuit 20, and fan motor 4 is connected to motor drive circuit 31.

As described above, in the air cleaner, the drive mode of ion generator 10 is switched to the monitor mode when the operation mode is set to the automatic mode and when the temperature and the humidity in the room attain the specific state. Temperature setting unit 155 and humidity setting unit 156 serve as input portions for setting threshold values used for determining the specific state. Temperature setting unit 155 and humidity setting unit 156 are implemented, for example, by a button switch or a slide switch provided in main unit 1 and serve to set the temperature and the humidity. Temperature setting unit 155 and humidity setting unit 156 may be provided in remote controller 130 so that the set temperature and humidity are transmitted from remote controller 130 to the air cleaner.

Motor drive circuit 31 switches the number of revolutions of fan motor 4 in 6 levels, in accordance with the instruction from control unit 150. In addition, voltage application circuit 20 drives ion generator 10 in accordance with the instruction from control unit 150.

Figure 17:
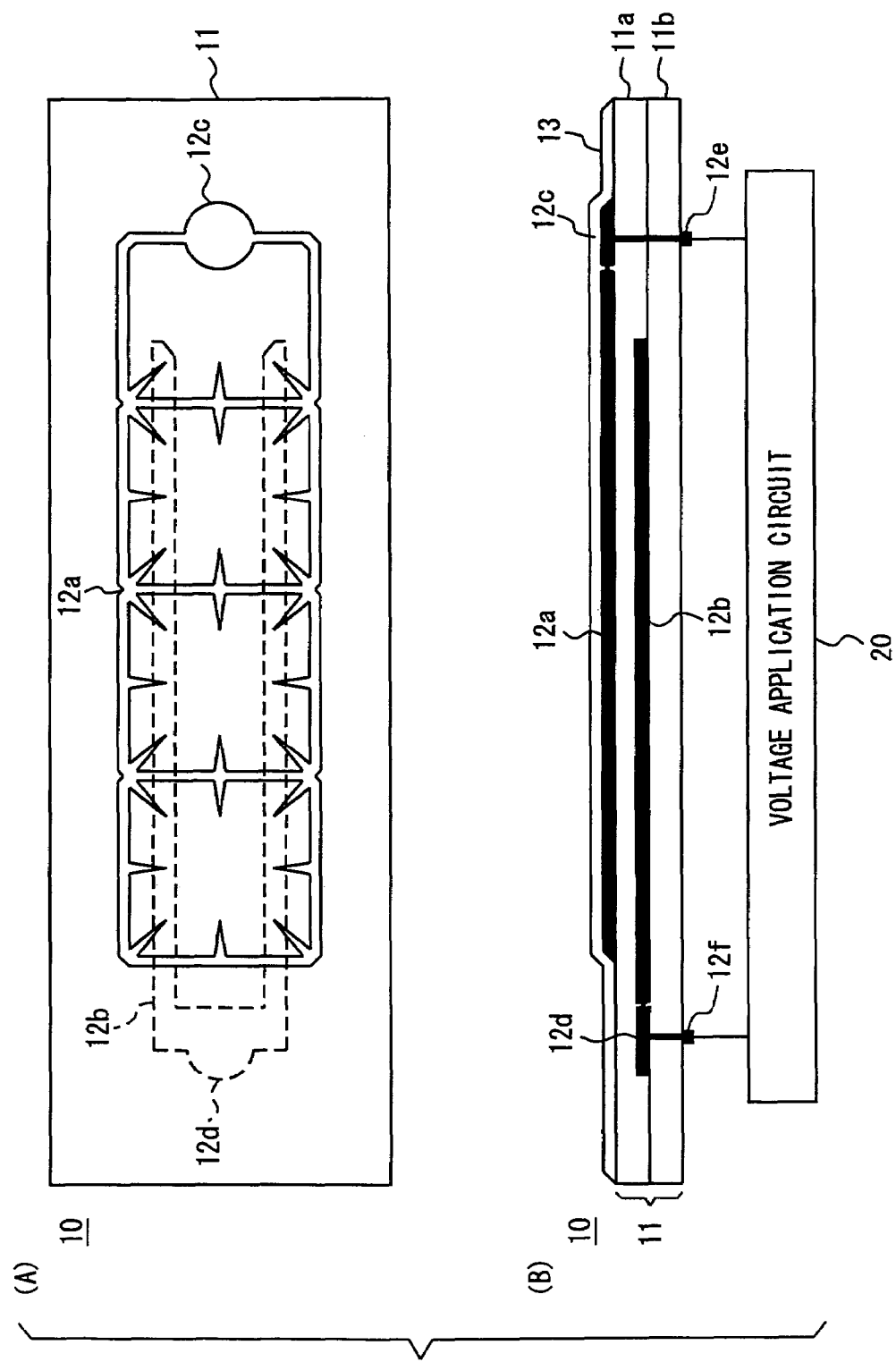
FIG. 17 is a schematic diagram of a configuration of the ion generator.

FIG. 17 schematically shows a configuration of the ion generator. FIG. 17(A) is a plan view of ion generator 10, while FIG. 17(B) is a side view of the same. Ion generator 10 includes a dielectric 11, a discharge electrode 12a, an induction electrode 12b, and a coating layer 13. When a voltage is applied to discharge electrode 12a and induction electrode 12b, discharge occurs between discharge electrode 12a and induction electrode 12b, whereby both positive and negative ions or negative ions are generated.

Dielectric 11 is implemented as a plate-like component formed by laminating an upper dielectric 11a and a lower dielectric 11b. Discharge electrode 12a is formed integrally with upper dielectric 11a on the surface of upper dielectric 11a. Induction electrode 12b is formed between upper dielectric 11a and lower dielectric 11b, and arranged in a manner facing discharge electrode 12a. Desirably, insulation resistance between discharge electrode 12a and induction electrode 12b is uniform, and discharge electrode 12a is parallel to induction electrode 12b.

In ion generator 10, discharge electrode 12a and induction electrode 12b are arranged on a surface and a back surface of upper dielectric 11a respectively, in a manner opposed to each other. Accordingly, a distance between discharge electrode 12a and induction electrode 12b can be constant. In this manner, a discharge state between discharge electrode 12a and induction electrode 12b is stabilized, and both positive and negative ions or negative ions can suitably be generated.

A discharge electrode contact 12e is electrically connected to discharge electrode 12a via a connection terminal 12c provided on the surface where discharge electrode 12a is located. One end of a conductive lead is connected to discharge electrode contact 12e while the other end thereof is connected to voltage application circuit 20, so that discharge electrode 12a and voltage application circuit 20 can electrically be connected. An induction electrode contact 12f is electrically connected to induction electrode 12b via a connection terminal 12d provided on the surface where induction electrode 12b is located. One end of a lead implemented by a copper wire is connected to induction electrode contact 12f while the other end thereof is connected to voltage application circuit 20, so that induction electrode 12b and voltage application circuit 20 can electrically be connected.

Figure 18:
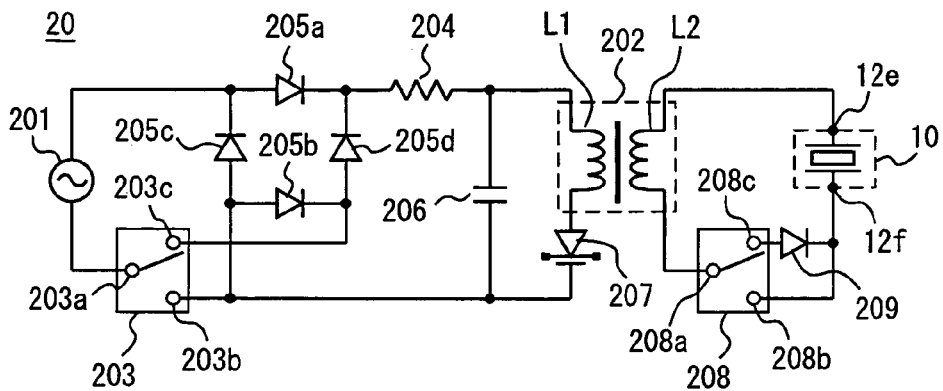
FIG. 18 is a circuit diagram of a voltage application circuit.

FIG. 18 is a circuit diagram of the voltage application circuit. Referring to FIG. 18, voltage application circuit 20 includes an AC power supply 201, a switching transformer 202, a switch relay 203, a resistor 204, diodes 205a to 205d, a capacitor 206, and an SIDAC® 207. SIDAC® 207 is one type of silicon control rectifier SCR and manufactured by Shindengen Electric Manufacturing Co., Ltd.

One end of AC power supply 201 is connected to the anode of diode 205a and the cathode of diode 205c, while the other end thereof is connected to a common terminal 203a of switch relay 203. The cathode of diode 205a is connected to one end of resistor 204 and the cathode of diode 205d. The other end of resistor 204 is connected to one end of a primary coil L1 of transformer 202 and one end of capacitor 206. The other end of primary coil L1 is connected to the anode of SIDAC® 207. The other end of capacitor 206 is connected to the cathode of SIDAC® 207, of which connection node is connected to one selection terminal 203b in switch relay 203 and respective anodes of diodes 205b and 205c. The cathode of diode 205b is connected to the anode of diode 205d, of which connection node is connected to the other selection terminal 203c of switch relay 203. One end of a secondary coil L2 of transformer 202 is connected to discharge electrode contact 12e of ion generator 10, while the other end thereof is connected to a common terminal 208a of a relay 208. One selection terminal 208c in relay 208 is connected to the anode of a diode 209, and the cathode of diode 209 is connected to induction electrode contact 12f. Induction electrode contact 12f of ion generator 10 is connected to the other selection terminal 208b in relay 208 and the anode of diode 209.

In voltage application circuit 20 configured as described above, when the drive mode of ion generator 10 is set to the clean mode in the normal state, selection terminal 203b is selected in switch relay 203 and selection terminal 208b is selected in switch relay 208.

Here, an output voltage of AC power supply 201 is subjected to half-wave rectification in diode 205a, then lowered by resistor 204, and applied to capacitor 206. When capacitor 206 is charged and a voltage across the capacitor attains a prescribed threshold value, SIDAC® 207 attains an on state and the charged voltage of capacitor 206 is discharged. Accordingly, a current flows through primary coil L1 in transformer 202 to transmit energy to secondary coil L2, whereby a pulse voltage is applied to ion generator 10. Immediately thereafter, SIDAC® 207 attains an off state and charge of capacitor 206 is started again.

By repeating charge and discharge described above, an AC impulse voltage in FIG. 19A (pp (Peak-to-Peak) value: 3.5 [kV], the number of times of discharge: 120 [times per second], for example) is applied between discharge electrode 12a and induction electrode 12b of ion generator 10. Here, corona discharge occurs in the vicinity of ion generator 10, and the ambient air is ionized. That is, $H^+(H_2O)_m$ which is a positive ion is generated when a positive voltage is applied, while $O_2^-(H_2O)_n$ which is a negative ion is generated when a negative voltage is applied (m, n represent 0 or any natural number). More specifically, when the AC voltage is applied between discharge electrode 12a and induction electrode 12b of ion generator 10, oxygen or moisture in the air is energized by electrolytic dissociation and ionized, whereby ions mainly containing $H^+(H_2O)_m$ (m represents 0 or any natural number) and $O_2^-(H_2O)_n$ (n represents 0 or any natural number) are generated. $H^+(H_2O)_m$ and $O_2^-(H_2O)_n$ are released to a space by means of the fan or the like and adhere to the surface of airborne fungi, followed by chemical reaction. As a result of chemical reaction, $H_2O_2$ or .OH which is an active species is generated. As $H_2O_2$ or .OH exhibits extremely strong activity, airborne fungi in the air are enclosed and inactivated. Here, .OH is a type of active species and represents radical OH.

Positive and negative ions chemically react on the surface of cells of the airborne fungi, as shown in expressions (1) to (3), resulting in generation of hydrogen peroxide ($H_2O_2$) or hydroxyl radical (.OH) which is active species. In expressions (1) to (3), m, m', n, and n' represent 0 or any natural number.

In this manner, airborne fungi are destroyed by decomposition action of the active species. Therefore, the fungi floating in the air can efficiently be inactivated and eliminated.

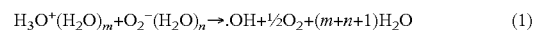

$$H_3O^+(H_2O)_m + O_2^-(H_2O)_n \rightarrow .OH + \tfrac{1}{2}O_2 + (m+n+1)H_2O \tag{1}$$

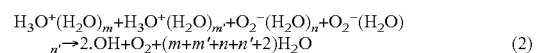

$$H_3O^+(H_2O)_m + H_3O^+(H_2O)_{m'} + O_2^-(H_2O)_n + O_2^-(H_2O)_{n'} \rightarrow 2.OH + O_2 + (m+m'+n+n'+2)H_2O \tag{2}$$

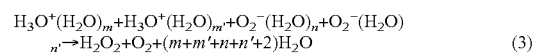

$$H_3O^+(H_2O)_m + H_3O^+(H_2O)_{m'} + O_2^-(H_2O)_n + O_2^-(H_2O)_{n'} \rightarrow H_2O_2 + O_2 + (m+m'+n+n'+2)H_2O \tag{3}$$

According to a mechanism described above, an effect to inactivate airborne fungi or the like can be obtained as a result of release of positive and negative ions shown above.

In addition, according to the expressions (1) to (3) above, the same action can also be achieved on a surface of a toxic substance in the air. Therefore, hydrogen peroxide ($H_2O_2$) or hydroxyl radical (.OH) which is active species oxidizes or decomposes the toxic substance, and transforms a chemical substance such as formaldehyde or ammonia to a harmless substance such as carbon dioxide, water or nitrogen, thereby rendering the toxic substance substantially harmless.

Therefore, fan motor 4 is driven so that positive and negative ions generated by ion generator 10 can be released to the outside of the main unit. An action of such positive and negative ions can inactivate molds and fungi in the air and suppress proliferation thereof.

In addition, the positive and negative ions also serve to inactivate viruses such as Coxsackie virus or polio virus, thereby preventing contamination due to introduction of these viruses. Furthermore, as it has been confirmed that the positive and negative ions serve to decompose molecules causing odor, the positive and negative ions can be utilized for deodorization of a space.

Wind was generated from turbo fan 5 toward ion generator 10, and an amount of positive ions and negative ions that arrived at an ion counter positioned approximately 25 cm away from ion generator 10 was measured. The ion counter counted approximately three hundred thousand (per cc), with regard to each of positive ion and negative ion.

Meanwhile, when the specific state is attained, the drive mode of ion generator 10 is set to the clean mode without exception. Here, selection terminal 203c is selected in switch relay 203, while selection terminal 208b is selected in switch relay 208.

Accordingly, the output voltage of AC power supply 201 is subjected to full-wave rectification in a diode bridge constituted of diodes 205a to 205d, then lowered by resistor 204, and applied to capacitor 206. Therefore, an AC impulse voltage of discharge frequency higher than when not in the specific state (pp value: 3.5 [kV], the number of times of discharge: 240 [times per second], for example) is applied between discharge electrode 12a and induction electrode 12b of ion generator 10, as shown in FIG. 19B.

Here, an amount of ions was measured under the condition described above. As a result, the ion counter counted approximately five hundred thousand per cc, with regard to each of positive ion and negative ion. That is, an amount of ions 1.7 times as large as that in the normal state, that is, when not in the specific state, was measured.

An operation the same as described above can be achieved also when the connection node of the cathode of diode 205b and the anode of diode 205d is connected to the other end of AC power supply 201 instead of switch relay 203, a switch is connected in series to the anode or the cathode of diode 205c or diode 205d, and the switch is controlled in accordance with the drive mode.

In addition, when ion generator 10 is in the ion control mode, selection terminal 203b is selected in switch relay 203, while selection terminal 208c is selected in switch relay 208.

Figure 19A:
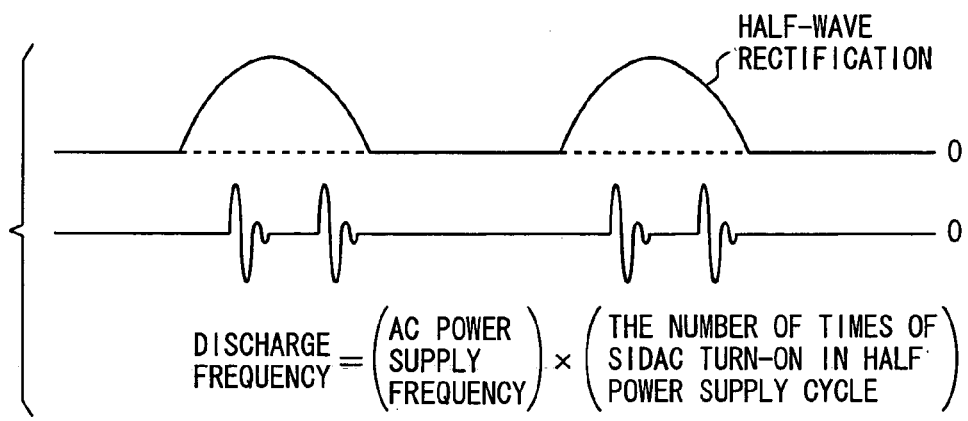
FIG. 19A is a diagram illustrating a voltage pulse output from the voltage application circuit.
Figure 19B:
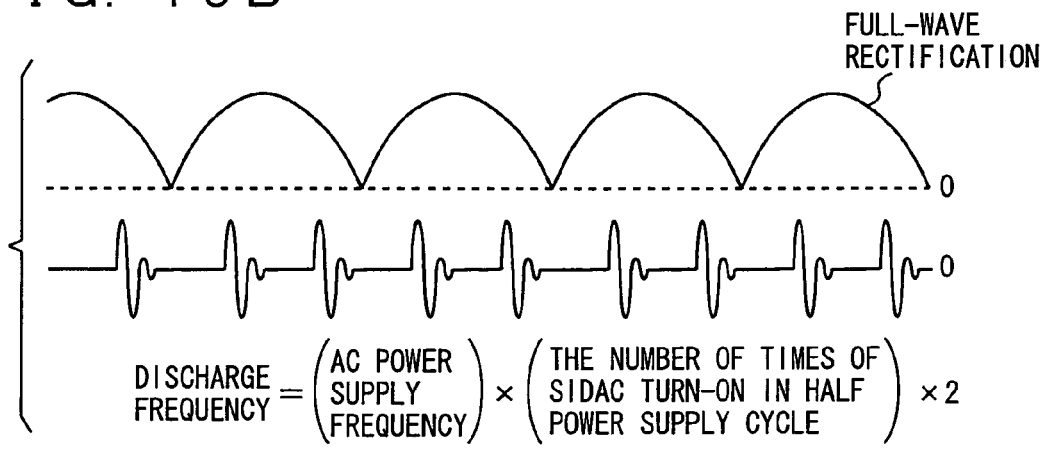
FIG. 19B is a diagram illustrating a voltage pulse output from the voltage application circuit.

As described above, as half-wave rectification is carried out by diode 209, solely a pulse of the negative voltage among the voltage application pulses shown in FIG. 19A is applied to ion generator 10. Consequently, corona discharge occurs in the vicinity of ion generator 10, and the ambient air is ionized. Here, as solely the negative voltage is applied, $O_2^-(H_2O)_n$ which is the negative ion is generated.

First Variation of Voltage Application Circuit

Figure 20:
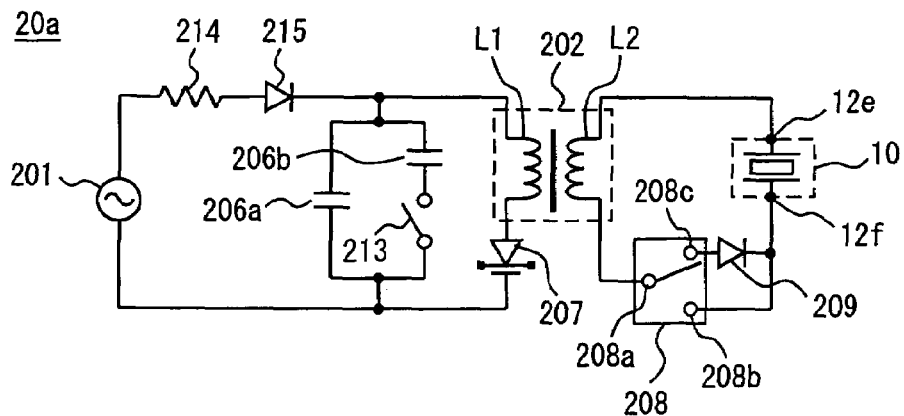
FIG. 20 is a circuit diagram of a variation of the voltage application circuit.

FIG. 20 is a circuit diagram of a variation of the voltage application circuit. Referring to FIG. 20, this voltage application circuit is different from voltage application circuit 20 in FIG. 18 in a circuit configuration between AC power supply 201 and primary coil L1 in switching transformer 202. As other circuits are the same, description thereof will not repeated. One end of AC power supply 201 is connected to one end of a resistor 214, while the other end of resistor 214 is connected the anode of a diode 215. The other end of AC power supply 201 is connected to the cathode of SIDAC® 207, one end of capacitor 106a, and one end of a relay 213. The cathode of diode 215 is connected to one ends of capacitors 206a, 206b and primary coil L1. The other end of capacitor 206b is connected to the other end of relay 213.

In a voltage application circuit 20a in the variation configured in the above-described manner, when the specific state is not attained, relay 213 closes. The output voltage of AC power supply 201 is subjected to half-wave rectification in diode 215, and thereafter applied to capacitors 206a and 206b. When capacitors 206a and 206b are charged and voltages across the capacitors attain a prescribed threshold value, SIDAC® 207 attains an on state and the charged voltages of capacitors 206a and 206b are discharged. Accordingly, a current flows through primary coil L1 in transformer 202 to transmit energy to secondary coil L2, whereby a pulse voltage is applied to ion generator 10. Immediately thereafter, SIDAC® 207 attains an off state and charge of capacitors 206a and 206b is started again.

On the other hand, when the specific state is attained, relay 213 opens. The output voltage of AC power supply 201 is subjected to half-wave rectification in diode 215, and applied solely to capacitor 206a. When capacitor 206a is charged and a voltage across the capacitor attains a prescribed threshold value, SIDAC® 207 attains an on state and the charged voltage of capacitor 206a is discharged. Accordingly, a current flows through primary coil L1 in transformer 202 to transmit energy to secondary coil L2, whereby a pulse voltage is applied to ion generator 10. Immediately thereafter, SIDAC® 207 attains an off state and charge of capacitor 206a is started again.

When relay 213 is open, the voltage applied to SIDAC® 207 attains the threshold value earlier than when it is closed. Therefore, the discharge frequency of the voltage pulse applied to ion generator 10 becomes higher when relay 213 is open than when it is closed. As the discharge frequency of the pulse applied to ion generator 10 is higher, an amount of generated ions increases. Therefore, solely by switching relay 213, an amount of ions generated from ion generator 10 can be switched.

Figure 21A:
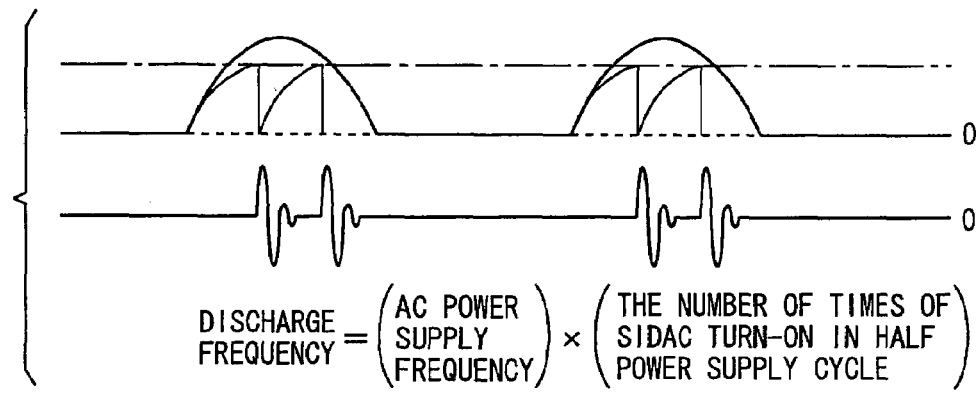
FIG. 21A is a diagram illustrating a voltage pulse output from the variation of the voltage application circuit.
Figure 21B:
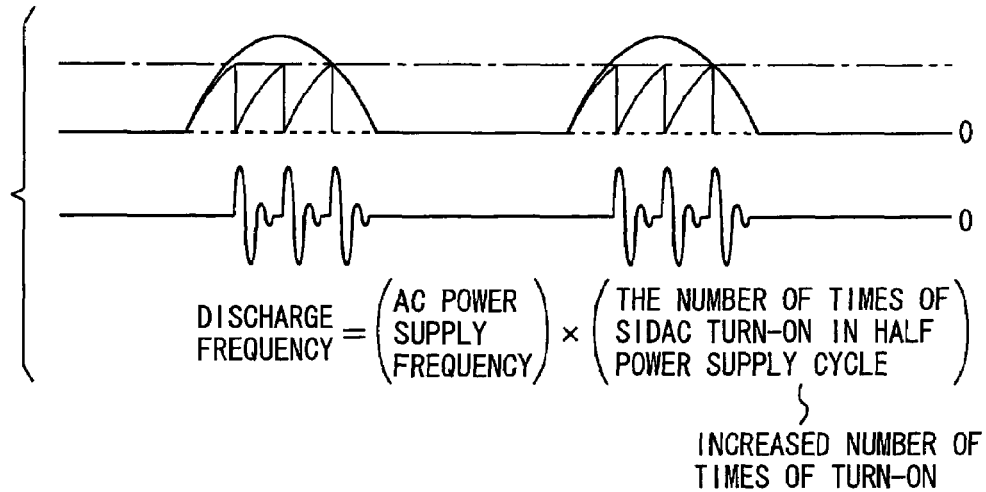
FIG. 21B is a diagram illustrating a voltage pulse output from the variation of the voltage application circuit.

FIGS. 21A and 21B show waveforms of voltages output from voltage application circuit 20a in the variation. FIG. 21A shows a waveform when relay 213 is closed, and illustrates a waveform of a voltage that has been subjected to half-wave rectification in diode 215 and a waveform of a voltage pulse applied to ion generator 10. FIG. 21B illustrates a waveform of a voltage that has been subjected to half-wave rectification when relay 213 is open and a waveform of a voltage pulse applied to ion generator 10

In voltage application circuit 20 described above, half-wave rectification and full-wave rectification have been switched by switching switch 203. Though solely an example of half-wave rectification has been described with regard to voltage application circuit 20a in the variation, switching between full-wave rectification and half-wave rectification may be employed. In such a case, when the voltage pulse of low discharge frequency is applied to ion generator 10, the voltage that has been subjected to half-wave rectification is used and relay 213 is closed. Meanwhile, when a voltage pulse of high discharge frequency is applied to ion generator 10, full-wave rectification is used and relay 213 is opened.

Second Variation of Ion Generator and Voltage Application Circuit

FIG. 22 shows variations of the ion generator. Referring to FIG. 22, an ion generator 10A in this variation is different from ion generator 10 described above in that it includes a first discharge portion 21 constituted of a discharge electrode 21a and an induction electrode 21b, and a second discharge portion 22 constituted of a discharge electrode 22a and an induction electrode 22b. In other words, ion generator 10A in this variation is different in including two discharge portions, that is, first discharge portion 21 and second discharge portion 22.

In ion generator 10A in this variation, induction electrodes 21b and 22b are formed on a surface of lower dielectric 11b, while discharge electrodes 21a and 22a are formed on a surface of upper dielectric 11a. The surface of upper dielectric 11a is covered with coating layer 13. In addition, upper dielectric 11a is stacked on the surface of lower dielectric 11b where induction electrodes 21b and 22b are formed. Discharge electrode 21a and induction electrode 21b in first discharge portion 21 are arranged in positions opposed to each other, while discharge electrode 22a and induction electrode 22b in second discharge portion 22 are arranged in positions opposed to each other.

In first discharge portion 21, connection terminal 21c of discharge electrode 21a is connected to discharge electrode contact 21e, which is connected to a voltage application circuit 20B via a lead. In addition, connection terminal 21d of induction electrode 21b is connected to induction electrode contact 21f, which is connected to voltage application circuit 20B via a lead.

Similarly, in second discharge portion 22, connection terminal 22c of discharge electrode 22a is connected to discharge electrode contact 22e, which is connected to voltage application circuit 20B via a lead. In addition, connection terminal 22*d* of induction electrode 22*b* is connected to induction electrode contact 22*f*, which is connected to voltage application circuit 20B via a lead.

Figure 23:
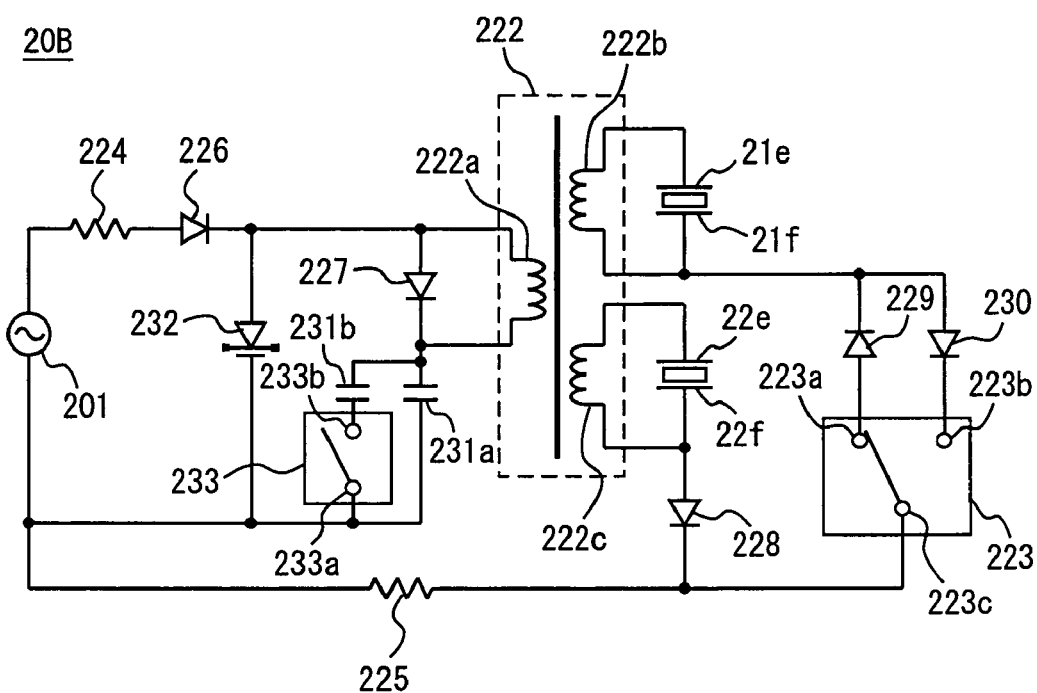
FIG. 23 is a circuit diagram of a voltage application circuit connected to the variation of the ion generator.
Figure 24:
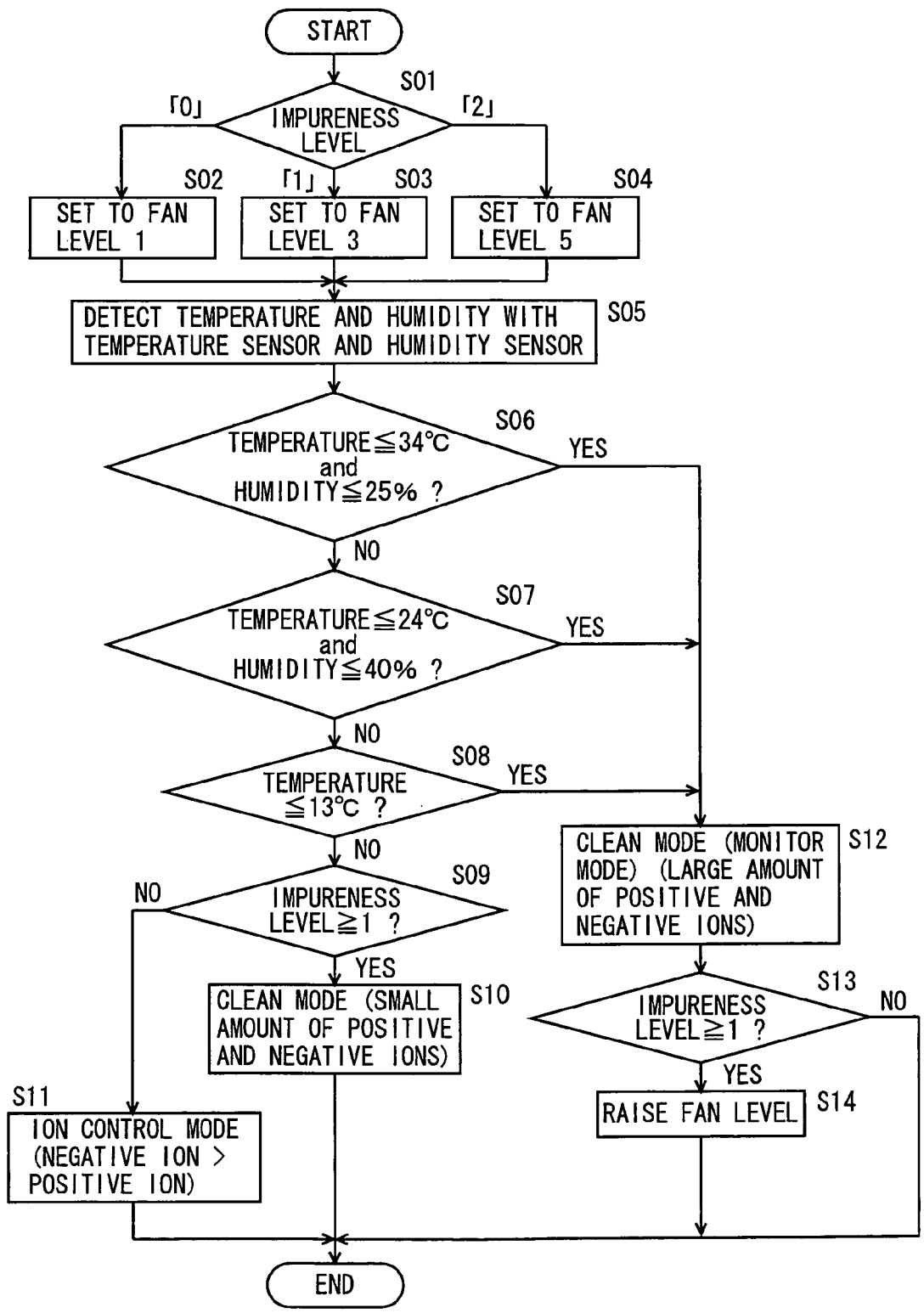
FIG. 24 is a flowchart showing processing performed in a control unit in the automatic mode.

FIG. 23 is a circuit diagram of voltage application circuit 20B connected to ion generator 10A in the variation. Referring to FIG. 23, voltage application circuit 20B includes AC power supply 201, a transformer 222, a switch relay 233, resistors 224, 225, diodes 226 to 230, capacitors 231*a*, 231*b*, and an SIDAC® 232.

One end of AC power supply 201 is connected to the anode of diode 226 via resistor 224. The cathode of diode 226 is connected to one end of a first coil 222*a* implementing a primary side of transformer 222, the anode of diode 227, and the anode of SIDAC® 232. The other end of first coil 222*a* is connected to the cathode of diode 227, of which connection node is connected to one ends of capacitors 231*a* and 231*b*. The cathode of SIDAC® 232, the other end of capacitor 231*a*, and one end 233*a* of relay 233 are connected to one another, of which connection node is connected to the other end of AC power supply 201. The other end 233*b* of relay 233 is connected to the other end of capacitor 231*b*.

One end of a second coil 222*b* implementing a secondary side of transformer 222 is connected to discharge electrode contact 21*e* of first discharge portion 21, while the other end of second coil 222*b* is connected to induction electrode contact 21*f* of first discharge portion 21, the cathode of diode 229, and the anode of diode 230. The anode of diode 229 is connected to one selection terminal 223*a* of switch relay 223, and the cathode of diode 230 is connected to the other selection terminal 223*b* of switch relay 223. One end of a third coil 222*c* implementing the secondary side of transformer 222 is connected to discharge electrode contact 22*e* of second discharge portion 22, while the other end of third coil 222*c* is connected to induction electrode contact 22*f* of second discharge portion 22 and the anode of diode 228. A common terminal 223*c* of switch relay 223 is connected to the cathode of diode 228, of which connection node is connected to the other end of AC power supply 201 via resistor 225.

In voltage application circuit 20B configured in the above-described manner, when the specific state is not attained and when the drive mode of ion generator 10 is set to the clean mode, relay 233 closes and selection terminal 223*a* is selected in switch relay 223. Here, a positive DC impulse voltage is applied between discharge electrode contact 21*e* and induction electrode contact 21*f* in first discharge portion 21, while a negative DC impulse voltage is applied between discharge electrode contact 22*e* and induction electrode contact 22*f* in second discharge portion 22. As a result of application of such voltages, corona discharge occurs in the vicinity of first discharge portion 21 and second discharge portion 22, and the ambient air is ionized. Here, $H^+(H_2O)_m$ which is a positive ion is generated in the vicinity of first discharge portion 21 to which the positive DC impulse has been applied, whereas $O_2^-(H_2O)_n$ which is a negative ion is generated in the vicinity of second discharge portion 22 to which the negative DC impulse has been applied (m, n represent 0 or any natural number).

In this manner, when selection terminal 223*a* is selected in switch relay 223, a substantially equal amount of positive ions and negative ions can be generated from first discharge portion 21 and second discharge portion 22 respectively. Therefore, positive and negative ions are caused to adhere to floating fungi or the like in the air, so that airborne fungi can be eliminated with decomposition action of generated hydrogen peroxide ($H_2O_2$) and/or hydroxyl radical (.OH) which is active species.

On the other hand, when the specific state is attained, relay 233 is opened and selection terminal 223*a* is selected in switch relay 223. In this case, solely capacitor 231*a* is charged. Therefore, a time period until the voltage applied to SIDAC® 232 attains the prescribed threshold value is shortened. Accordingly, discharge frequencies of the positive DC impulse voltage applied to first discharge portion 21 and the negative DC impulse voltage applied to second discharge portion 22 are increased. In this manner, a larger amount of positive ions is generated in first discharge portion 21, and a larger amount of negative ions is generated in second discharge portion 22.

When the specific state is not attained and when the drive mode of ion generator 10 is set to the ion control mode, relay 233 is closed and selection terminal 223*b* is selected in switch relay 223.

In such a case, the negative DC impulse voltage is applied to both first discharge portion 21 and second discharge portion 22. When such a negative DC impulse voltage is applied, $O_2^-(H_2O)_n$ which is a negative ion (n represents 0 or any natural number) is generated in the vicinity of both first discharge portion 21 and second discharge portion 22.

As described above, when selection terminal 223*b* is selected in switch relay 223, solely negative ions can be generated from both first discharge portion 21 and second discharge portion 22. Therefore, ion balance can be adjusted so as to create a state in which negative ions are dominant, thereby enhancing relaxation effect.

FIG. 24 is a flowchart showing processing performed in the control unit in the automatic mode. Referring to FIG. 24, initially, the fan level is set based on the impureness level (steps S01 to S04). At step S01, the impureness level is determined. If the impureness level is determined as "0", fan level 1 is set (step S02). If the impureness level is determined as "1", fan level 3 is set (step S03). If the impureness level is determined as "2", fan level 5 is set (step S04).

Thereafter, whether or not the specific state is attained is determined (steps S05 to S08). If it is determined that the specific state is attained, the process proceeds to step S12. If it is determined that not the specific state but the normal state is attained, the process proceeds to step S09. Specifically, at step S05, the temperature and the humidity are detected by temperature sensor 151 and humidity sensor 152 (step S05). If it is determined at step S06 that the temperature is not higher than 34° C. and the humidity is not higher than 25%, it is determined that the specific state is attained and the process proceeds to step S12. Otherwise, the process proceeds to step S07. If it is determined at step S07 that the temperature is not higher than 24° C. and the humidity is not higher than 40%, it is determined that the specific state is attained and the process proceeds to step S12. Otherwise, the process proceeds to step S08. If it is determined at step S08 that the temperature is not higher than 13° C., it is determined that the specific state is attained and the process proceeds to step S12. Otherwise, the process proceeds to step S09.

If it is determined that the normal state is attained, whether or not the impureness level attains to 1 or higher is determined at step S09. If YES, the process proceeds to step S10. If NO, the process proceeds to step S11. At step S10, the drive mode of ion generator 10 is set to the clean mode. This clean mode is not the monitor mode. Therefore, an amount of positive and negative ions generated from ion generator 10 is smaller than in the monitor mode. At step S11, the drive mode of ion generator 10 is set to the ion control mode. Here, ion generator 10 generates negative ions in an amount larger than that of positive ions.

If it is determined that the specific state is attained, the drive mode of ion generator 10 is set to the clean mode at step S12. This clean mode is the monitor mode. Therefore, an amount of positive and negative ions generated from ion generator 10 is larger than when not in the monitor mode. At step S13, whether or not the impureness level attains to 1 or higher is determined. If YES, the process proceeds to step S14. If NO, the process ends. At step S14, the fan level set at steps S02 to S04 is raised. Specifically, fan level 3 is raised to fan level 4, and fan level 5 is raised to fan level 6. The fan level is raised to increase an amount of air that passes through humidifying filter 41. Therefore, an amount of water supplied to ion generator 10 is increased. Consequently, the residual period of generated ions is extended and sterilizing effect is improved.

As described above, in the air cleaner according to the present embodiment, humidifying filter 41 is arranged in the path from inlet port 2*a* to outlet port 6*a*, 6*b* at a position closer to inlet port 2*a* than ion generator 10. Therefore, humidified air is supplied to ion generator 10. When the impureness level attains to 1 or higher and the specific state is attained, water is supplied to ion generator 10 in an amount larger than in the normal state. Ions are surrounded by water molecules, whereby its residual period is extended. Therefore, the sterilizing effect can be improved.

In addition, fan motor 4 is controlled to raise the fan level, so that water supplied to ion generator 10 is increased. The structure is thus simplified.

Moreover, in the specific state, ion generator 10 driven in the clean mode is driven in the monitor mode in which ions are generated in an amount larger than in the normal state. Therefore, a larger amount of ions can be released to the room.

If the temperature and the humidity in the room attain the specific state, monitor indicator light 115 illuminates. Therefore, the user can know that the room is in the non-preferable environment where viruses are likely to proliferate. At this time point, the user operates operation switch button 104 of his/her own will, to switch the operation mode to the automatic mode. Then, in the air cleaner, the drive mode of ion generator 10 is set to the monitor mode in the clean mode and the fan level is raised. Higher concentration of positive and negative ions in the room can thus be achieved of user's own will.

Although the present invention has been described and illustrated in detail, it is clearly understood that the same is by way of illustration and example only and is not to be taken by way of limitation, the spirit and scope of the present invention being limited only by the terms of the appended claims.

The invention claimed is:

1. An air conditioning apparatus, comprising:
   an ion generation portion for generating ions, arranged in a path from an inlet port to an outlet port;
   a humidifying portion for humidifying air around said ion generation portion, arranged in said path at a position closer to the inlet port than said ion generation portion;
   an impureness detection portion for detecting impureness of air;
   a temperature and humidity detection portion detecting temperature and humidity; and
   a humidified state varying unit for varying a degree of humidification by said humidifying portion in accordance with a degree of impureness detected by said impureness detection portion; wherein
   said humidified state varying unit increases the degree of humidification of the air around said ion generation portion by said humidifying portion in accordance with the degree of impureness detected by said impureness detection portion when impureness is detected by said impureness detection portion and when the temperature and the humidity detected by said temperature and humidity detection portion attain a prescribed state, and does not vary the degree of humidification of the air around said ion generation portion by said humidifying portion when impureness is not detected by said impureness detection portion even though the temperature and the humidity detected by said temperature and humidity detection portion attain said prescribed state.

2. The air conditioning apparatus according to claim 1, wherein
   said humidifying portion includes
   a blowing portion for causing air to flow such that the air taken in through the inlet port exits through the outlet port,
   a tray for holding water, and
   a filter partially immersed in the water held in said tray, and
   said humidified state varying unit controls said blowing portion to raise a fan level.

3. The air conditioning apparatus according to claim 1, wherein
   when impureness is detected by said impureness detection portion and when the temperature and the humidity detected by said temperature and humidity detection portion attain said prescribed state, said humidified state varying unit controls said ion generation portion to generate ions in an amount larger than when said prescribed state is not attained.

4. The air conditioning apparatus according to claim 3, wherein
   said prescribed state includes a second state in which viruses are likely to proliferate.

5. The air conditioning apparatus according to claim 1, further comprising:
   a state notification portion for notification of said detected temperature and/or said detected humidity; and
   an instruction accepting portion for accepting an instruction to start control of said humidifying portion; wherein
   said humidified state varying unit starts control in response to acceptance of the instruction by said instruction accepting portion.

6. The air conditioning apparatus according to claim 1, wherein
   said ion generation portion generates positive and negative ions.

7. The air conditioning apparatus according to claim 1, wherein
   said impureness detection portion includes a dust sensor.

8. The air conditioning apparatus according to claim 1, wherein
   said impureness detection portion includes an odor sensor.

9. The air conditioning apparatus according to claim 1, further comprising a cleaning portion for lowering impureness level of air.

* * * * *